(12) United States Patent
Perrier et al.

(10) Patent No.: US 6,197,757 B1
(45) Date of Patent: Mar. 6, 2001

(54) PARTICLES, ESPECIALLY MICROPARTICLES OR NANOPARTICLES, OF CROSSLINKED MONOSACCHARIDES AND OLIGOSACCHARIDES, PROCESSES FOR THEIR PREPARATION AND COSMETIC, PHARMACEUTICAL OR FOOD COMPOSITIONS IN WHICH THEY ARE PRESENT

(76) Inventors: Eric Perrier, Quartier St Martin, 38138 les Cotes d'Arey; Sylvie Rey-Goutenoire, les Varines, 69420 les Haies; Chantal Buffevant, les Carrés, 69390 Millery; Marie-Christine Levy, 18 Ter rue Houzeau-Muiron; Nadine Pariot, 14, rue Saint Léonard, both of 51100 Reims; Florence Edwards, 5-7, rue de la Belle aumône, 02160 Longueval; Marie-Christine Andry, 221, avenue du Général Leclerc, 51530 Dizy, all of (FR)

( * ) Notice: Subject to any disclaimer, the term of this patent is extended or adjusted under 35 U.S.C. 154(b) by 0 days.

(21) Appl. No.: 09/350,131

(22) Filed: Jul. 9, 1999

(30) Foreign Application Priority Data

Jul. 9, 1998 (FR) .................................................. 98 0889

(51) Int. Cl.$^7$ .............................. A61K 31/70; C07H 1/00; C07H 3/00
(52) U.S. Cl. ................................. 514/53; 514/23; 514/54; 536/1.11; 536/103; 536/123.13; 536/124
(58) Field of Search .................................. 536/1.11, 103, 536/123.13, 124; 514/23, 53, 54

(56) References Cited

FOREIGN PATENT DOCUMENTS

| 0555980 A1 | * | 8/1993 | (EP) . |
| WO 93/17784 | | 9/1993 | (WO) . |
| WO 95/07689 | | 3/1995 | (WO) . |

* cited by examiner

*Primary Examiner*—Elli Peselev

(57) ABSTRACT

Particles comprising an outer wall formed of one or more saccharide components selected from the group consisting of monosaccharides and oligosaccharides crosslinked by interfacial crosslinking in emulsion, preferably at room temperature, with a polyfunctional acylating crosslinking agent to produce ester linkages between the acylatable hydroxyl group(s) of the primary alcohol(s) of the saccharide component and the acyl groups of the polyfunctional acylating agent. These particles can be used for the manufacture of cosmetic, pharmaceutical and food compositions.

80 Claims, 4 Drawing Sheets

PARTICLES, ESPECIALLY MICROPARTICLES OR NANOPARTICLES, OF CROSSLINKED MONOSACCHARIDES AND OLIGOSACCHARIDES, PROCESSES FOR THEIR PREPARATION AND COSMETIC, PHARMACEUTICAL OR FOOD COMPOSITIONS IN WHICH THEY ARE PRESENT

FIELD OF INVENTION

The present invention relates essentially to particles, especially microparticles or nanoparticles, of crosslinked monosaccharides and oligosaccharides, to processes for their preparation and to cosmetic, pharmaceutical or food compositions in which they are present. These particles are advantageously of small dimensions. In addition, these particles are advantageously used for the incorporation or encapsulation of various hydrophilic or lipophilic substances and particularly substances which can be used in the pharmaceutical, cosmetic and food sectors.

Within the framework of the present description and the claims, the words "particle(s) of small dimensions" denote both microparticles and nanoparticles and the words "microparticles" or "nanoparticles" relate both to microspheres or nanospheres and to microcapsules or nanocapsules.

Furthermore, the words "microspheres" or "nanospheres" refer to particles which have an essentially uniform structure throughout the whole of their bulk, while the words "microcapsules" or "nanocapsules" refer to particles which have a crosslinked wall surrounding an internal core or space filled with a solid, gelled, liquid or gaseous medium.

STATE OF THE ART

The encapsulation of active substances in particles offers valuable advantages such as, for example, protection of the encapsulated substance or its slow release at the site of use for a prolonged effect.

If the particles are intended for use in the cosmetic, pharmaceutical or food sectors, they must consist of biocompatible materials such as proteins and polysaccharides.

The preparation of microcapsules from polysaccharides, i.e. high-molecular carbohydrates, has been widely described in the prior art literature (cf., for example, P. B. Deasy: Microencapsulation and related processes, Drugs and the Pharmaceutical Sciences, vol. 20, 1984, Marcel Dekker).

In particular, these compounds can be used by themselves in microencapsulation processes based on simple coacervation, or associated with polycationic polymers in processes based on the formation of polyelectrolyte complexes.

Microcapsules have also been prepared by the interfacial crosslinking of polysaccharides by means of polyfunctional isocyanates, as described for example in document FR-A-2 275 250, which relates to microcapsules prepared from hydroxypropyl cellulose, or in document U.S. Pat. No. 4,138,362, which applies to natural gums or chitosan.

Furthermore, microcapsules with a wall formed of co-crosslinked glycosaminoglycans and collagen are described in document FR-A-2 642 329, which relates to the application of interfacial crosslinking by means of diacid chlorides to mixtures of glycosaminoglycans and collagen.

Interfacial crosslinking by means of diacid chlorides in emulsion systems has also been applied to the preparation of particles from polysaccharides in document EP-0 630 287 B1 equivalent to U.S. Pat. No. 5,562,924, the reaction pH values used not exceeding 10.

In these various processes for the preparation of microcapsules, the carbohydrates used are polysaccharides, i.e. molecules with high molecular weights above 5000 daltons, which consist of an association of a large number of oside units. In fact, it is well known that macromolecules like proteins and poly-saccharides have special adsorption properties at interfaces; cf., for example, pages 317 to 335 of the following work: "Functional properties of food macromolecules", edited by Mitchell J. R. and Ledward D. A., Elsevier, London, 1986. These adsorption phenomena at interfaces, which result in the formation of an interfacial film, are a particularly favorable factor in the preparation of particles by the interfacial crosslinking of biopolymers such as polysaccharides.

As regards carbohydrates with molecular weights below 5000 daltons, the prior art literature contains processes for the preparation of polymer beads from cyclodextrins, which are cyclic oligosaccharides having a hydrophobic cavity capable of trapping various molecules of compatible geometry. The most widely employed crosslinking agent is epichlorohydrin, as for example in the article by Wiedenhof N. et al. (Die Stärke, 1969, 21, 119–123).

As far as the use of acid dichlorides is concerned, document U.S. Pat. No. 3,472,835 describes the preparation of cyclodextrin resins by crosslinking in a homogeneous medium (DMF or DMSO). However, the preparative conditions are drastic, the reaction taking place at 100° C. for a prolonged period of time (6 h). Moreover, the substances to be trapped do not easily diffuse into these compact beads. Proposals have been made to improve the porosity of the polymers, either by generating a release of $CO_2$ in situ (in document U.S. Pat. No. 4,958,015) or by carrying out the crosslinking on the surface of a porous mineral oxide (U.S. Pat. No. 4,902,788). Document U.S. Pat. No. 4,902,788 indicates (p. 3, column 3, lines 54–55) that the principal disadvantage of aromatic acid dichlorides is that they give relatively low yields of resin.

Thus the prior art neither describes nor suggests the preparation of particles by the interfacial crosslinking of monosaccharides or oligosaccharides, such as cyclodextrins, by means of acid dichlorides in emulsion systems.

OBJECTS OF THE INVENTION

One main object of the invention is to solve a new technical problem consisting in the provision of biocompatible and biodegradable, stable particles which optionally incorporate various hydrophilic or lipophilic substances and can be used in the pharmaceutical, cosmetic and food sectors.

A further main object of the invention is to solve a new technical problem consisting in the provision of biocompatible and biodegradable particles by a particularly simple manufacturing method affording particles of constant quality, preferably from substances of perfectly defined chemical composition, which also are advantageously capable of being dissolved, particularly in an aqueous phase at room temperature.

One main object of the present invention is to solve a new technical problem consisting in the provision of novel biocompatible and biodegradable particles of small dimensions from monosaccharides and oligosaccharides.

A further object of the present invention is to solve a new technical problem consisting in the provision of a solution for the preparation of stable particles of small dimensions from monosaccharides and oligosaccharides, while at the same time optionally allowing the encapsulation of one or more active substances in the form of a solution, suspension or emulsion.

A further object of the present invention is to solve a new technical problem consisting in the provision of a solution for the preparation, from cyclodextrins, particularly β-cyclodextrins, of novel biocompatible and biodegradable, insoluble particles of small dimensions which can easily be isolated from a liquid medium and have retained the specific trapping capacity of these cyclodextrins.

A further object of the present invention is to solve a new technical problem consisting in the provision of a solution for the preparation, from cyclodextrins, particularly β-cyclodextrins, of novel biocompatible and biodegradable, porous, insoluble particles of small dimensions which can easily be loaded with various active molecules and then incorporated into larger particles, which are also biocompatible and biodegradable, so as to allow a slower and sustained release of the active molecule by diffusion through the material of said larger particle.

A further object of the present invention is to solve a novel technical problem consisting in the provision of a solution for the preparation of a product from dihydroxyacetone (DHA) which, when incorporated into a composition, does not impair its stability, particularly its color stability, and which, when applied to the skin, will release the DHA, the latter being capable of combining with the amino acids in the skin to produce a pigmentation.

A further object of the present invention is to prevent any degradation of a composition containing DHA, in particular any modification of its color with time.

A further object of the present invention is to solve a new technical problem consisting in the provision of a solution for the preparation of stable particles of small dimensions from oligosaccharides or monosaccharides, or polyols or amino sugars derived therefrom, which are capable of releasing the starting compound by enzymatic hydrolysis, thereby constituting a special type of precursor capable of slowly releasing a compound with a valuable biological activity.

A further object of the present invention is to solve a new technical problem consisting in the provision of a solution for the preparation of stable particles of small dimensions from heterosides whose oside moiety contains one or more oside molecules, which are capable of releasing the heteroside by enzymatic hydrolysis, thereby constituting a special type of precursor or prodrug.

A further object of the present invention is to solve the above-mentioned new technical problems by means of simple manufacturing processes which can be used on the industrial scale, particularly in the cosmetic, pharmaceutical or food industry. This solution should preferably make it possible to prepare particles of small dimensions whose size can be adjusted at will, particularly over a range of dimensions from a nanometer to more than a millimeter and especially from about 10 nanometers to about 2 mm.

A further main object of the invention is to solve the above-mentioned new technical problems with starting compounds which are perfectly harmless and inexpensive, thereby allowing wide use by the pharmaceutical, cosmetic and food industries.

SUMMARY OF THE INVENTION

Thus, according to the present invention, it has been discovered, totally unexpectedly, that it is possible to obtain stable particles, especially microparticles or nanoparticles, from monosaccharides or oligosaccharides by initiating an interfacial crosslinking reaction between a monosaccharide or an oligosaccharide and a polyfunctional acylating crosslinking agent, particularly a diacid halide and preferably a diacid chloride, at the interface of the phases of an emulsion, particularly of the "water-in-oil" type, preferably at room temperature.

In one particularly advantageous embodiment, these particles can be manufactured by first emulsifying an alkaline aqueous phase containing the monosaccharide or oligosaccharide in a hydrophobic phase, preferably at room temperature, and then adding the solution of crosslinking agent to the emulsion. It is then found that membranes consisting of crosslinked molecules of the carbohydrate are formed at the interface of the aqueous droplets due to the creation of ester linkages between the crosslinking agent and hydroxyl groups of the monosaccharide or oligosaccharide.

The invention also makes it possible to prepare particles of great value by the interfacial crosslinking of monosaccharides and oligosaccharides by means of difunctional acylating agents in emulsion systems, preferably at room temperature. In fact, monosaccharides and oligosaccharides are substances of perfectly defined chemical composition, and hence of constant quality, which, unlike high-molecular polysaccharides, do not incur the risk of a variation in composition between manufacturers and between product batches. Furthermore, in contrast to polysaccharides, which often are not readily soluble in the aqueous phases usable in these processes and often require the aqueous phase to be heated in order to dissolve, monosaccharides like glucose and oligosaccharides like lactose or sucrose are very soluble in water at room temperature. It may be added that many of these compounds, such as sucrose or lactose, are widely used in the food industry and are available at relatively low cost. Also, these compounds are perfectly harmless.

They therefore appear in general terms to be capable of yielding biocompatible and biodegradable particles, incorporating various hydrophilic or lipophilic substances, which can be used in the pharmaceutical, cosmetic and food sectors.

Furthermore, the interfacial crosslinking of some of these compounds can make it possible to achieve specific objects such as:

the stabilization of a degradable substance, as in the case of dihydroxyacetone (DHA), which gives colored degradation products with time, and/or the preparation of a precursor in particulate form which is capable of releasing an active form following enzymatic attack, for example:

DHA, which is capable of combining with the amino acids in the skin to impart a pigmentation thereto, or a heteroside, such as saponoside or streptomycin, in the case where the oside moiety of the heteroside, which consists of one or more oside molecules containing at least one primary alcohol group, has made it possible to prepare particles by interfacial crosslinking.

It is pointed out that the principle of ester precursors of active molecules has been developed in therapeutics for drugs intended for application to the skin (Viala K. H. et al., Drug Dev. Ind. Pharm., 1985, 11, 1133–1173) or in cosmetology (Forestier J. P., Int. J. Cosmetic Sci., 1992, 14, 47–63).

or the preparation of porous insoluble particles of cyclodextrins which open up specific applications based on the trapping of molecules in order to remove them from a liquid medium, harvest them or release the trapped molecule slowly at the site of action.

Now, if the conditions described in the prior art documents such as document EP-0 630 287 B 1, applying to polysaccharides, are applied to monosaccharides or oligosaccharides, i.e. if the interfacial crosslinking is carried out with acid dichlorides in emulsion systems where the pH of the aqueous phase used to dissolve the carbohydrates does not exceed 9.8, it is not possible to obtain stable particles. The particles are obtained with a zero or very low yield and microscopic examination shows copious debris indicative of the high fragility of the crosslinked material.

Within the framework of the invention it has been discovered, totally unexpectedly, that it is possible to obtain stable particles, especially microparticles or nanoparticles, of crosslinked oligosaccharides or monosaccharides by using an alkaline aqueous phase with a pH above 10 to dissolve the carbohydrates and initiating the polycondensation reaction by means of a dihalide, particularly an acid dichloride, at the interface of an emulsion.

The particles obtained are sufficiently stable to withstand prolonged incubation in an oven at 45° C., in the form of an aqueous suspension, without their structure being destroyed. They are also sufficiently stable to undergo lyophilization without their structure being destroyed, and resume a spherical shape after rehydration, this being yet another decisive technical advantage of the invention.

The particles are progressively destroyed after incubation in human plasma, which demonstrates their biodegradability, particularly under the action of esterases.

Depending on the chosen conditions of emulsification, the particle size can vary from less than 1 micrometer, i.e. nanometer size, obtained for example by using a high-pressure homogenizer, to several hundred micrometers and even to more than 1 mm.

It has also been discovered that it is possible to obtain particles by initiating the polycondensation reaction in an emulsion of the "oil-in-water" type. In this case a hydrophobic phase containing a crosslinking agent, preferably a diacid halide and particularly a diacid chloride, is emulsified in an alkaline aqueous phase containing the monosaccharide or oligosaccharide, used as the continuous phase. The reaction is allowed to develop at the interface and agitation is maintained for a suitable time. It is found that a membrane forms around the dispersed hydrophobic droplets to give particles with hydrophobic contents, consisting in this case of capsules.

DETAILED DESCRIPTION OF THE INVENTION

According to a first feature, the present invention covers particles which comprise, at least on the surface, a wall formed of one or more monosaccharides or oligosaccharides crosslinked by means of interfacial crosslinking in emulsion, preferably at room temperature, between the monosaccharide(s) or oligosaccharide(s), comprising at least one primary alcohol group, and a polyfunctional acylating crosslinking agent, preferably a diacid halide and particularly a diacid chloride, so as to produce ester linkages between the acylatable hydroxyl group(s) of the primary alcohol(s) of the monosaccharide or oligosaccharide and the acyl groups of the polyfunctional acylating agent.

Within the framework of the invention, any monosaccharide or oligosaccharide with a molecular weight below 5000 daltons, carrying at least one primary alcohol group, can be used without limitation. Likewise, any polyfunctional crosslinking agent containing at least two acylating groups can be used without limitation.

In one advantageous embodiment of the invention, it is possible to use monosaccharide or oligosaccharide derivatives such as polyols resulting from hydrogenation of the aldehydic or ketonic groups of oses, aldonic acids derived from aldoses, and corresponding lactones, phosphoric acid esters of oses, osamines, or heterosides whose oside moiety consists of one or more oses and contains at least one primary alcohol group.

In one advantageous embodiment of the invention, the above-mentioned particles can be prepared from a single low-molecular monosaccharide or oligosaccharide or from mixtures.

In another advantageous embodiment of the invention, the above-mentioned monosaccharides can be ketoses such as dihydroxyacetone (DHA), erythrulose, ribulose, xylulose, fructose and sorbose, as well as derivatives thereof.

In another advantageous embodiment of the invention, the above-mentioned monosaccharides can be aldoses such as erythrose, threose, xylose, arabinose, ribose, deoxyribose, glucose, mannose and galactose, as well as derivatives thereof.

The monosaccharide derivatives which can be used, by themselves or in mixtures, in the processes according to the invention include especially the corresponding polyols such as sorbitol, mannitol, xylitol, arabitol, dulcitol, lactitol, galactitol, erythritol and threitol, amino sugars such as glucosamine, galactosamine, glucosamine sulfate and galactosamine sulfate, and aldonic acids or lactones such as gluconic acid, galactonic acid, gluconolactone and galactonolactone. Commercial preparations containing polyols, for example Néosorb 70® ("sorbitol 70%", Roquette), also belong to this group.

The oligosaccharides which can be used, by themselves or in mixtures, in the processes according to the invention include disaccharides such as, in particular, sucrose, lactose, maltose, cellobiose, trehalose and melibiose, oligosaccharides such as raffinose, dextrins, or products of the partial hydrolysis of starch, cyclodextrins such as alpha-cyclodextrin, beta-cyclodextrin and gamma-cyclodextrin, cyclodextrin derivatives such as hydroxyethyl β-cyclodextrin and hydroxypropyl β-cyclodextrins (2-HP-β-CD, 3-HP-β-CD, 2,3-HP-β-CD), branched cylodextrins such as glucosyl β-CD, diglucosyl β-CD, maltosyl β-CD and dimaltosyl β-CD, or mixtures of oligosaccharides, for example the products marketed under the name Glucidex® by Roquette, containing variable proportions of glucose, maltose and maltodextrins.

The oligosaccharide derivatives which can be used, by themselves or in mixtures, in the processes according to the invention include especially the corresponding polyols such as maltitol and lactitol, or commercial preparations containing polyols and obtained by hydrogenating products of the partial hydrolysis of starch.

The monosaccharide and oligosaccharide derivatives also include hetero-sides or glycosides, i.e. molecules consisting of an oside moiety linked to a non-oside moiety. The heterosides which can be used in the processes according to the invention have an oside moiety containing one or more oside units and at least one primary alcohol group. The non-oside or aglycone fraction preferably has a cyclic structure containing one or more aromatic or non-aromatic rings which can include one or more heteroatoms such as nitrogen, oxygen or sulfur atoms.

The heterosides which can be used in the processes according to the invention include especially β-D-xylosides such as 4-methylumbelliferyl β-D-xyloside and p-nitrophenyl β-D-xyloside, riboflavin, natural nucleosides consisting of ribonucleosides such as guanosine, adenosine, uridine and cytidine, or deoxyribonucleosides such as deoxyguanosine, deoxyadenosine, deoxycytidine and thymidine, synthetic antiviral or anticancer nucleosides, structural analogs of natural nucleosides, such as adenosine analogs and deoxycytidine analogs, mononucleotides, deoxymononucleotides, oligonucleotides, deoxyoligonucleotides, antibiotics of the aminoglycoside group, such as streptomycin, dihydrostreptomycin, kanamycins, amikacin, dibekacin, tobramycin, neomycins and paromomycin, saponosides with steroidal aglycone, such as saponosides from ivy, saponosides with triterpene aglycone, such as the saponoside from Panama bark, or cardiotonic heterosides with steroidal aglycone, such as digitoxin.

In another advantageous embodiment of the invention, the present invention also covers particles which comprise, at least on the surface, a wall formed of cyclodextrins, particularly crosslinked β-cyclodextrins.

The inventors have discovered, particularly unexpectedly, that the particles prepared from cyclodextrins retain a valuable trapping capacity, are easily separated from the media containing the substance to be trapped, and can be re-used after the trapped substance has been discharged. Thus, if it is desired to remove a constituent of a mixture by complexation, the use of said insoluble form will make it possible easily to separate the complex off and even to discharge the complexed molecule from the insoluble form of cyclodextrin so that it can be re-used.

Thus, in another advantageous embodiment of the invention, the particles of crosslinked cyclodextrins according to the invention can be impregnated or loaded with an active substance, particularly a cosmetically active substance, a pharmaceutically active substance, a dietetically active substance, an agri-foodstuff substance or an agri-industrial substance. This impregnation or loading with said active substance or active principle can take place very simply. For example, the particles of crosslinked cyclodextrins are immersed or incubated in a solution containing the active principle for a sufficient time to allow the particles to become impregnated or loaded with, or to trap, at least some of the active principle. The pH of the aqueous solution of active principle is close to neutrality or slightly acid and must not exceed 8, i.e. it is preferably between about 4.5 and 8, so as to avoid hydrolysis of the ester linkages and degradation of the particles.

This impregnation or loading with active substances or active principles produces a system which slowly releases this active substance or active principle out of the system.

This slow or delayed release can be further improved in the following manner.

Thus, in yet another advantageous embodiment of the invention, the particles of crosslinked cyclodextrins according to the invention, loaded with active principle, can be enclosed in larger particles formed of a crosslinked protein or a mixture of co-crosslinked proteins and polysaccharides to give a slow release system. In this case these particles are manufactured by initially preparing particles of crosslinked cyclodextrins according to the invention. These particles are then incubated in a solution of active principle for a sufficient time to allow some of the active principle to be trapped by the particles, as has just been described above for the trapping or loading of an active substance or active principle in the particles of crosslinked cyclodextrins.

Proteins or a mixture of protein and polysaccharide are then dissolved in the suspension of crosslinked particles and the resulting mixture is used as the aqueous phase for the preparation of particles by interfacial crosslinking of the protein or protein/polysaccharide mixture, in an emulsion of the water-in-oil type, by means of an acid dihalide, preferably a dichloride, according to the Applicant's previous patents, for example patent U.S. Pat. No. 5,395,620 or patent FR-A-97 08968. The mixture is then dispersed in a hydrophobic phase to give an emulsion, an acid dihalide, preferably a dichloride, is then added to the emulsion and the reaction is allowed to develop for a sufficient time for larger particles to form around the particles of previously crosslinked cyclodextrins according to the invention by acylation of the acylatable functional groups of the protein or protein/polysaccharide mixture. This ultimately gives larger particles containing the intact particles of crosslinked cyclodextrins according to the invention and active principle partially complexed by particles of crosslinked cyclodextrins. The crosslinked material constituting the larger particles will allow a slow release of the active principle out of the system.

As regards the proteins which can advantageously be used within the framework of the invention, there may be mentioned animal proteins such as collagen, atelocollagen, gelatin, serum albumin, ovalbumin, hemoglobin, milk proteins including casein and whey proteins, lactalbumin, globulins and fibrinogen; and vegetable proteins extracted especially from Leguminosae and particularly from the following plants: soya, lupin, pea, chick pea, alfalfa, horse bean, lentil, haricot bean, colza and sunflower, or from cereals like wheat, maize, barley, malt, oats and rye. As regards the polysaccharides which can advantageously be used, preference is given to glycosaminoglycans, advantageously including chondroitin 4-sulfate, chondroitin 6-sulfate, dermatan sulfate, heparan sulfate and keratan sulfate, as well as heparin and derivatives thereof, particularly low-molecular heparin with a molecular weight of between about 2000 and 10,000, and cosmetically or pharmaceutically acceptable heparin salts such as the sodium and calcium salts, natural gums, carrageenans, glucomannans, galactomannans, amylose or amylopectin or mixtures thereof, and hydroxyalkylated polysaccharide derivatives such as hydroxyethyl starch or hydroxyethyl cellulose.

In another advantageous embodiment of the invention, the present invention also covers particles which comprise, at least on the surface, a wall formed of crosslinked cyclodextrins, particularly β-cyclodextrins, loaded with an active substance and enclosed in larger biocompatible and biodegradable particles, for example particles of crosslinked proteins or co-crosslinked proteins and polysaccharides, so as to form a slow release system.

To manufacture these particles in this case, a protein, optionally together with a polysaccharide, is added to a suspension of cyclodextrin particles in the solution of active substance and this aqueous phase is used to manufacture particles by interfacial crosslinking according to the Applicant's previous patents, for example patent U.S. Pat. No. 5,395,620 or patent FR-A-97 08968.

It is known that cyclodextrins are cyclic oligosaccharides formed of 6 to 8 glucose units. These molecules have valuable properties associated with the hydrophobicity of their internal cavity. In particular, they can increase the solubility in water of active principles (this being the case especially of β-cyclodextrins and hydrophilic derivatives thereof) and can trap various molecules and thus stabilize them against heat, oxidation, light and evaporation (examples being essential oils, flavorings and liposoluble vitamins).

Furthermore, some cyclodextrin derivatives afford a sustained or delayed release of the trapped molecule (Uekama K. et al. in: New Trends in Cyclodextrins and Derivatives, edited by D. Duchêne, Editions de Santé, Paris, 1991, chap. 12, 411–446). This is the case especially of hydrophobic β-cyclodextrin derivatives such as diethyl and triethyl β-cyclodextrins, which reduce the aqueous solubility of very water-soluble active principles (sustained release), and of ionizable β-cyclodextrin derivatives such as carboxymethyl ethyl β-cyclodextrin, a compound which is sparingly soluble in acid media and whose solubility increases with pH through ionization of the carboxymethyl groups (release prevented in the gastric medium and delayed until the intestine is reached).

However, these derivatives are relatively expensive compared with the initial cyclodextrins. As far as the initial cyclodextrins are concerned, their solubility in water presents a problem if it is desired to use them in a release system which is to be in contact with water, this solubility making it difficult to control the release of the complexed molecule (Friedman R. B. in: New Trends in Cyclodextrins and Derivatives, edited by D. Duchêne, Editions de Santé, Paris, 1991, chap. 4, 157–177). Likewise, the solubility in water impedes the isolation of the complexes when it is desired specifically to remove one constituent from a mixture in an aqueous medium, and the recovery of the free cyclodextrins when it is desired to recycle them commercially.

The preparation of polymers containing cyclodextrins provides a solution to these problems. Thus the slower release of an active substance can be achieved by complexing it with a polymer carrying β-cyclodextrins and by placing a dialysis membrane between the polymer and the release medium. Thus, for example, Behar N. et al. (S.T.P. Pharma, 1987, 3, 237–247) show that, when placed in a dialysis tube, synthetic polymers, one of them water-soluble (polyethylene-imine) and the other insoluble (prepared from polyvinyl chloroformate), carrying cyclodextrin molecules and loaded with a very water-soluble active substance like propranolol, make it possible to slow down the diffuision of the active principle into the outer aqueous compartment, the polymer and the complex being unable to pass through the membrane.

Unexpectedly, the inventors have also been able to observe the same phenomenon in dialysis experiments performed with propranolol in the presence of perfectly biocompatible and biodegradable particles of crosslinked cyclodextrins according to the present invention.

Following the same principle, Fenyvesi E. (J. Inclusion Phenom., 1988, 6, 537–545) reports that a system consisting of microcapsules containing an active principle complexed with a soluble cyclodextrin polymer makes it possible to delay the release of the active principle, the polymer being unable to pass through the membrane of the microcapsules.

The inventors have also succeeded in achieving this remarkable result with perfectly biocompatible microcapsules of crosslinked protein containing methylene blue complexed with increasing amounts of particles of crosslinked β-cyclodextrins. In vitro release experiments show a slowing-down of the release compared with microcapsules not containing cyclodextrin particles. The slowing-down becomes more pronounced as the amount of encapsulated cyclodextrin particles increases.

The inventors have also shown that particles of crosslinked DHA are perfectly stable while at the same time allowing a pigmentation to appear after application to the skin, demonstrating that they are biodegradable and are capable of regenerating the base substance with its specific activity intact after enzymatic degradation.

According to a second feature, the present invention covers a process for the manufacture of particles of small dimensions comprising, at least on the surface, a wall formed of one or more crosslinked monosaccharides or oligosaccharides, said process comprising:

a) the preparation of an aqueous phase at a pH of between 10.5 and about 14, in which at least one monosaccharide or at least one oligosaccharide is dissolved;

b) the preparation of a hydrophobic phase essentially immiscible with water and optionally containing a surfactant;

c) the dispersion of the aqueous phase in the hydrophobic phase by agitation so as to form an emulsion of the water-in-oil type;

d) the addition, to the emulsion, of a solution of a polyfunctional acylating agent, agitation being maintained for a sufficient period of time to crosslink the monosaccharide or oligosaccharide at the interface of the dispersed droplets of said emulsion and thereby to form particles; and e) optionally the separation of said particles from the reaction medium.

The present invention also covers a process for the manufacture of particles of small dimensions comprising, at least on the surface, a wall formed of one or more crosslinked monosaccharides or oligosaccharides, said process comprising:

a) the preparation of an aqueous phase at a pH of between 10.5 and about 14, in which at least one monosaccharide or at least one oligosaccharide is dissolved;

b) the preparation of a hydrophobic phase essentially immiscible with water and containing a polyfunctional acylating crosslinking agent;

c) the dispersion of the hydrophobic phase in the aqueous phase by agitation so as to form an emulsion of the oil-in-water type, agitation being maintained for a sufficient period of time to crosslink the monosaccharide or oligosaccharide at the interface of the dispersed droplets of said emulsion and thereby to form particles, especially capsules; and d) optionally the separation of said particles from the reaction medium.

The present invention also covers a process for the manufacture of particles of crosslinked cyclodextrins of small dimensions enclosed in larger particles, said process comprising the following steps:

a) Firstly particles of crosslinked cyclodextrins according to the invention are prepared in an emulsion system of the water-in-oil type and are recovered.

b) These particles are then placed or incubated in an aqueous solution of an active principle with a pH of between about 4.5 and about 8 for a sufficient time to allow the active principle to be trapped by the particles.

c) A protein or a protein/polysaccharide mixture is then dissolved in the suspension of particles.

d) The mixture is dispersed by agitation in a hydrophobic phase to give an emulsion of the water-in-oil type.

e) A solution of a polyfunctional acylating agent is added to the emulsion, agitation being maintained for a sufficient time for larger particles to form around the particles of crosslinked cyclodextrins according to the invention by acylation of the acylatable functional groups of the protein or protein/polysaccharide mixture.

f) Optionally the larger particles obtained, containing the intact particles of crosslinked cyclodextrins according to the invention and active principle partially complexed by the cyclodextrins of the particles of crosslinked cyclodextrins, are separated off.

In one advantageous embodiment of the invention, this aqueous solution can consist of a buffer such as a carbonate or phosphate buffer adjusted to a pH above 10.5, for example to pH 11, or a solution of an alkaline agent such as sodium hydroxide, for example 1 M sodium hydroxide solution.

In one advantageous embodiment of the invention, the concentration of monosaccharide or oligosaccharide in the aqueous phase is between 3% and 80%, preferably between 10 and 30%.

In another advantageous embodiment of the invention, the above-mentioned polyfinctional acylating crosslinking agent preferably consists of at least one acid dihalide preferably selected from the group comprising phthaloyl, terephthaloyl, sebacoyl, glutaryl, adipoyl and succinyl dihalides, or an anhydride of these acids. It is preferable to use a dichloride of these acids.

In another advantageous embodiment of the invention, the above-mentioned microcapsules are prepared by interfacial crosslinking, preferably at room temperature, from an emulsion whose disperse phase to be encapsulated contains one or more water-soluble, liposoluble or insoluble active substances incorporated in the form of a solution, suspension or emulsion.

According to a third feature, the present invention also covers the use of these particles.

The general applications of the particles of crosslinked monosaccharides and oligosaccharides are as follows:

In the fields of cosmetics, pharmaceutics and food, these biocompatible and biodegradable particles allow the incorporation of water-soluble or liposoluble substances in the form of solutions, suspensions or emulsions.

The particles according to the invention have a particular additional value in cosmetics; this is associated with the release in situ, after hydrolysis, of the base constituent, which may have a desired specific activity on the skin, for example the moisturizing effect of monosaccharides and disaccharides (lactose) and the polyols derived therefrom (mannitol, sorbitol), a stimulating effect on glycosaminoglycan synthesis and an antiwrinkle effect (glucosamine sulfate, galactosamine sulfate, beta-xyloside derivatives).

Attention may also be drawn to the value of encapsulating hydrophobic droplets in a very hydrophilic membrane consisting, for example, of crosslinked sorbitol or sucrose.

The applications of the particles of crosslinked cyclodextrins are as follows:

As such, unloaded, for removing a constituent from a medium in the form of an inclusion complex:

for technological applications such as the separation of stereoisomers, the catalysis of chemical reactions and the extraction of bitter molecules, caffeine, cholesterol and phenylalanine. The particles can thus constitute a solid adsorbent to be used, for example, for packing columns through which the liquid to be purified will be passed.

for the detoxification of biological or non-biological liquid media and water, especially for the extraction of aromatic amines, phenols, bilirubin and toxins. The biocompatibility of the particles is an important advantage here.

for the recovery of a substance from a liquid medium.

for analytical applications, the particles making it possible to improve the detection of substances by concentrating them.

in the field of cosmetics, where the trapping properties of cyclodextrins can be utilized to absorb the excess lipids on the skin (dulling effect) or to absorb the degradation compounds of perspiration (deodorant products) or the substances responsible for bad breath (anti-bad breath effect in toothpastes or mouthwashes). The biocompatibility of the particles is again an important advantage here.

Loaded with active substances in the form of inclusion complexes and incorporated in slow diffusion systems, particularly in particles and especially particles of crosslinked proteins or co-crosslinked proteins and polysaccharides:

in the field of cosmetology for a slower and sustained release of the active substance, enabling the action to be prolonged, with an improvement in the skin tolerance towards active principles having an irritating effect, for example retinoic acid, salicylic acid, etc.

in the field of therapeutics for the manufacture of drugs or pharmaceutical compositions with a slower and sustained release of the active substance, enabling the action to be prolonged, by any mode of administration and with an improvement in the skin and mucosa tolerance.

The applications of the particles of crosslinked DHA are associated with the stabilization of the DHA, allowing incorporation into a variety of cosmetic preparations and releasing the DHA after enzymatic degradation on the surface of the skin, said DHA being capable of combining with the amino acids in the skin to give a pigmentation.

The particles of crosslinked heterosides have applications associated especially with the fact that they represent novel precursors of particulate type:

which can be used in cosmetics for the slow release, by enzymatic degradation of the particle, of the constituent heteroside, which will then exert its specific activity (example: particles of crosslinked saponoside), and which can be used in therapeutics, in which case the particles constitute a novel type of particulate vector or prodrug simultaneously allowing:

protection of the active principle and a slow release of the constituent heteroside by enzymatic degradation of the particle, for a prolonged effect and/or an improvement in the bioavailability and/or an improvement in the skin or mucosa tolerance, and targeting associated with the particulate nature of the prodrug.

Depending on the size of the particles, it will be possible, for example, to prepare particles with a diameter of between about 10 and 100 $\mu$m, for example of about 15 $\mu$m, from an antibiotic like streptomycin; after intravenous injection, these particles can make it possible to target the capillaries of the lung according to a known principle of vectorization by capillary blocking (Davis S. S. and Illum L., Acta Pharm. Technol., 1986, 32, 4–9) and to release the antibiotic slowly in situ for an improved efficacy. Alternatively, nanoparticles of active substance will be prepared which will be picked up by the cells, particularly the cells of the reticuloendothelial system, and will enable diseases such as bacterial or parasitic diseases to be treated with said active substance.

As a further alternative, the preparation of particles of nanometer size from oligonucleotides or oligodeoxynucleotides can directly afford a vectorized and stable form of these oligonucleotides or oligodeoxynucleotides which can pass directly into the cells and is capable of releasing the initial oligonucleotide or oligodeoxynucleotide inside the cell, especially for use in the context of antiviral or anticancer therapy or in the context of gene therapy, or for use in the general context of the transfection of cells or transfer of genetic material, thereby avoiding the use of viral vectors or synthetic vectors.

As a further alternative, the preparation of particles of nanometer size from antiviral or anticancer nucleosides can directly afford a vectorized and stable form of these nucleosides which can pass directly into the cells and is capable of releasing the initial nucleoside inside the cell.

According to a fourth feature, the present invention also covers a composition, selected especially from the group consisting of a cosmetic composition, a pharmaceutical composition and a food composition, which comprises, as one of its components or active principles, the above-mentioned particles comprising, at least on the surface, a wall formed of one or more monosaccharides or oligosaccharides crosslinked particularly by means of interfacial crosslinking in emulsion, preferably at room temperature, between the monosaccharide(s) or oligosaccharide(s), comprising at least one primary alcohol group, and a polyfunctional acylating crosslinking agent, preferably a diacid halide and particularly a diacid chloride, so as to produce ester linkages between acylatable hydroxyl groups of the primary alcohol(s) of the monosaccharide or oligosaccharide and the acyl groups of the polyfunctional acylating agent.

Other characteristics of these particles are apparent from the foregoing description and from the following description relating to the Examples.

According to a fifth feature, the present invention also covers a method of cosmetic or therapeutic treatment which comprises the application, to an appropriate site on a mammal, preferably a human being, of a cosmetically or therapeutically effective amount of the above-mentioned particles comprising, at least on the surface, a wall formed of one or more monosaccharides or oligosaccharides crosslinked particularly by means of interfacial crosslinking in emulsion, preferably at room temperature, between the monosaccharide(s) or oligosaccharide(s), comprising at least one primary alcohol group, and a polyfunctional acylating crosslinking agent, preferably a diacid halide and particularly a diacid chloride, so as to produce ester linkages between acylatable hydroxyl groups of the primary alcohol (s) of the monosaccharide or oligosaccharide and the acyl groups of the polyfunctional acylating agent.

Other characteristics of these particles are clearly apparent from the foregoing and following description, especially with reference to the Examples and likewise to the cosmetic or therapeutic uses indicated above, particularly with regard to the description of the second feature.

In one particular embodiment, the present invention relates to a method of cosmetic treatment for a mammal, preferably a human being, which comprises the topical application, to a zone of the skin, scalp or hair in question, of particles as defined above and especially particles which can also contain at least one cosmetically active substance.

In one advantageous embodiment, the invention also covers a method of therapeutic treatment which comprises the application, to an appropriate site on a mammal, preferably a human being, of a therapeutically effective amount of the above-mentioned particles comprising, at least on the surface, a wall formed of crosslinked cyclodextrins, particularly β-cyclodextrins, loaded with an active substance and enclosed in larger biocompatible and biodegradable particles such as particles of crosslinked proteins or co-crosslinked proteins and polysaccharides, these double particles constituting a slow release system which can be administered by any mode of administration, such as the oral, parenteral, rectal, vaginal, pulmonary, cutaneous, ophthalmic or nasal route.

In one advantageous embodiment, the invention also covers a method of therapeutic treatment which comprises the application, to an appropriate site on a mammal, preferably a human being, of a therapeutically effective amount of the above-mentioned particles comprising, at least on the surface, a wall formed of one or more crosslinked heterosides, said particles behaving as particulate prodrugs or precursors of the active heteroside(s) and being capable of releasing the active principle in vivo under the action of enzymes such as esterases, which particles can be administered by any mode of administration, such as the oral, parenteral, rectal, vaginal, pulmonary, cutaneous, ophthalmic or nasal route, and allow protection of the active principle, slow release, improvement of the bioavailability, improvement of the skin or mucosa tolerance, targeting towards an organ, a tissue or a vascular territory, or, in the case of nanoparticles, passage of the active principle into the target cells for an antibiotic, antiviral or anticancer therapy or for the transfer of genetic material into cells.

Other objects, characteristics and advantages of the invention will become clearly apparent from the following explanatory description referring to several Examples of the invention, which are given simply by way of illustration and cannot therefore in any way limit the scope of the invention, and referring to the attached Figures, in which:

Figure 1:
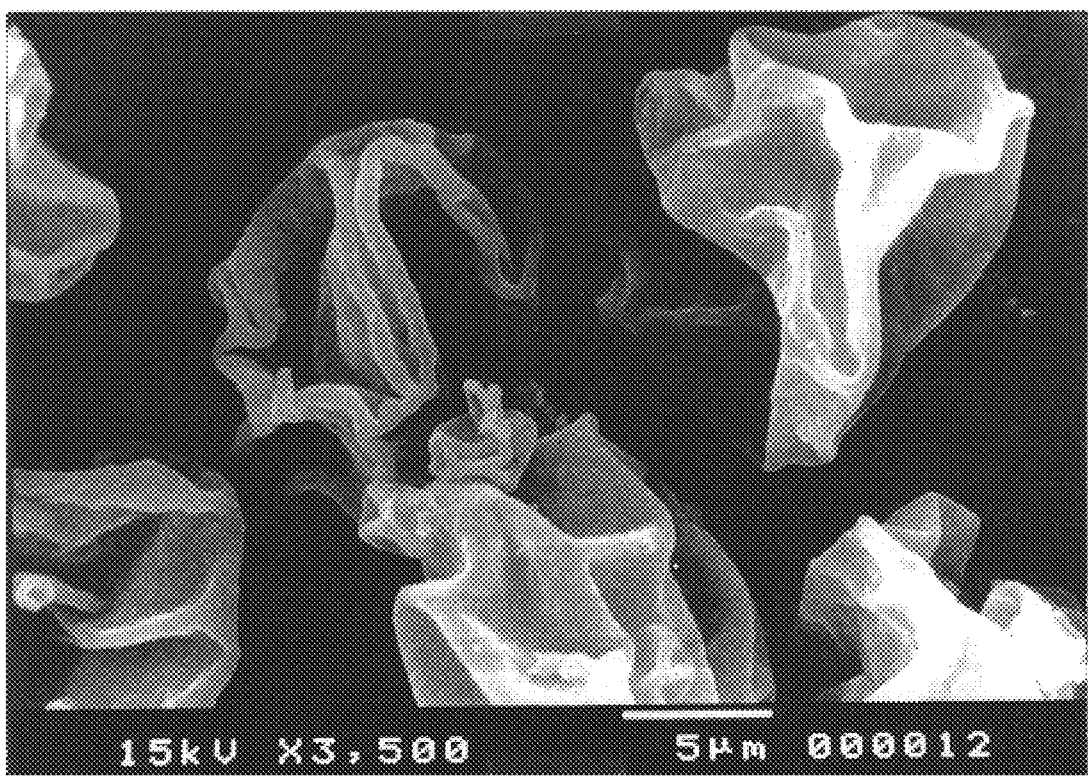
FIG. 1 shows a scanning electron microscope negative of particles of the invention prepared from β-cyclodextrins at a concentration of 10% using a speed of agitation of 2000 rpm, with reference to Example 7.

In the following Examples, all the percentages are given by weight, unless indicated otherwise. Likewise, unless indicated otherwise, the temperature is room temperature and the pressure is atmospheric pressure.

EXAMPLE 1

Standard Protocol for the Preparation of Particles of Crosslinked Oligosaccharides or Monosaccharides in an Emulsion System of the "Water-In-Oil" Type a) A 10% solution of oligosaccharide or monosaccharide in 1 M sodium hydroxide solution is prepared.

b) 6 ml of this solution are emulsified in 30 ml of cyclohexane containing 5% of Span 85 by mechanical agitation for 5 min at a speed of 2000 rpm.

c) Without stopping the agitation, 40 ml of a 5% solution of terephthaloyl chloride in a 1:4 (v/v) chloroform/cyclohexane mixture are added to the emulsion and agitation is continued for 30 min. When the reaction has ended, the reaction medium is diluted by the addition of 40 ml of cyclohexane and agitation is continued for 2–3 min.

d) The microcapsules are then separated off by natural decantation or by centrifugation.

e) The sediment is washed by successive resuspension in different media, namely cyclohexane, 95% ethanol with 2% of Tween 20 added, 95% ethanol and distilled water.

This protocol was successfully applied to the following compounds (Sigma, unless indicated otherwise), which are given as examples:

Ex. 1.1. β-Cyclodextrins
Ex. 1.2. Dextrins (Glucidex 40® or Glucidex 47®, Roquette)
Ex. 1.3. Raffinose
Ex. 1.4. Cellobiose
Ex. 1.5. Sucrose
Ex. 1.6. Maltose
Ex. 1.7. Lactose
Ex. 1.8. Trehalose
Ex. 1.9. Dihydroxyacetone (DHA)
Ex. 1.10. D-Fructose
Ex. 1.11. Sorbose
Ex. 1.12. D-Ribose
Ex. 1.13. D-Deoxyribose
Ex. 1.14. D-Xylose
Ex. 1.15. Paranitrophenyl beta-D-xyloside
Ex. 1.16. D-Arabinose
Ex. 1.17. D-Glucose
Ex. 1.18. D-Mannose
Ex. 1.19. D-Galactose
Ex. 1.20. Xylitol
Ex. 1.21. Erythritol
Ex. 1.22. Arabitol
Ex. 1.23. Sorbitol
Ex. 1.24. Mannitol
Ex. 1.25. Dulcitol (galactitol)
Ex. 1.26. Maltitol
Ex. 1.27. Gluconic acid
Ex. 1.28. Gluconolactone
Ex. 1.29. D-Glucosamine
Ex. 1.30. D-Galactosamine
Ex. 1.31. D-Glucosamine sulfate
Ex. 1.32. D-Galactosamine sulfate
Ex. 1.33. Saponin from soapbark
Ex. 1.34. Guanosine
Ex. 1.35. Streptomycin sulfate
Ex. 1.36. Riboflavin
Ex. 1.37. Deoxyribonucleic acid (DNA) from herring sperm (crude oligonucleotides)
Ex. 1.38. Uridine
Ex. 1.39. Lactitol Spherical microparticles with a size of between a few micrometers and a few tens of micrometers (20 to 90 µm) were obtained.

EXAMPLE 2

Variants of the Preparation of Particles of Crosslinked Oligosaccharides or Monosaccharides in an Emulsion System of the "Water-In-Oil" Type 1) The concentration of oligosaccharide or monosaccharide in the aqueous phase can vary between 2% and 80%.

2) The 1 M sodium hydroxide solution can be replaced with sodium hydroxide solutions or solutions of another alkaline agent, such as potassium hydroxide, which are more concentrated (2 M, 5 M etc.) or more dilute, or with buffers brought to a pH above 10, for example a carbonate or phosphate buffer of pH 11.

3) The oligosaccharide or monosaccharide used is preferably selected from the group of compounds given in Example 1 and consisting of β-cyclodextrin, dextrins, raffinose, disaccharides such as, in particular, cellobiose, sucrose, maltose, lactose and trehalose, monosaccharides comprising ketoses such as dihydroxyacetone (DHA), fructose and sorbose, or aldoses such as ribose, deoxyribose, xylose, arabinose, glucose, mannose and galactose, oligosaccharide or monosaccharide derivatives comprising, in particular, the corresponding polyols such as maltitol, commercial preparations containing polyols and obtained by hydrogenating products of the partial hydrolysis of starch, xylitol, erythritol, arabitol, sorbitol, mannitol, dulcitol, lactitol or galactitol, amino sugars such as glucosamine, acids or lactones derived therefrom, such as gluconic acid and gluconolactone, heterosides such as saponin, antibiotics such as streptomycin, riboflavin, guanosine or adenosine, or oligonucleotides or oligodeoxynucleotides.

The following can also be used:

other cyclodextrins such as alpha-cyclodextrin and gamma-cyclodextrin, cyclodextrin derivatives such as hydroxyethyl β-cyclodextrin and hydroxypropyl β-cyclodextrins (2-HP-β-CD, 3-HP-β-CD, 2,3-HP-β-CD), and branched cyclodextrins such as glucosyl β-CD, diglucosyl β-CD, maltosyl β-CD and dimaltosyl β-CD, mixtures of oligosaccharides, for example the products marketed by Roquette under the name Glucidex®, containing variable proportions of glucose, maltose and maltodextrins, commercial preparations containing polyols, for example Neosorb 70® ("sorbitol 70%", Roquette), deoxyribonucleosides such as deoxyguanosine and deoxycytidine, synthetic antiviral or antitumoral nucleosides, structural analogs of natural nucleosides, such as adenosine and deoxyadenosine analogs and cytidine and deoxycytidine analogs, mononucleotides and oligonucleotides, and monodeoxynucleotides and oligodeoxynucleotides.

4) The hydrophobic phase can consist of another organic solvent or mixture of solvents, fixed oils such as 2-ethylhexyl cocoate, or other mixtures well known to those skilled in the art. The nature and percentage of the surfactant added can also vary.

5) The particle size is adjusted by varying the nature and percentage of the surfactant and/or the speed of agitation. It can be 1 µm or less for speeds of rotation of 15,000–20,000 rpm.

EXAMPLE 3

Stability Experiments on Particles of Crosslinked Oligosaccharides or Monosaccharides in an Emulsion System of the "Water-In-Oil" Type Experimental Procedure:

Samples of particles suspended in distilled water are placed in an oven at 45° C. The samples are observed at regular intervals in order to detect any change in color and appearance and to check the limpidity of the supernatant. The integrity of the particles is monitored by microscopic examination.

Results:

The following particles were studied:

Particles of:

crosslinked β-cyclodextrins according to Example 1.1.

crosslinked sucrose according to Example 1.5.

crosslinked DHA according to Example 1.9.

crosslinked fructose according to Example 1.10.

crosslinked mannitol according to Example 1.24.

crosslinked glucosamine according to Example 1.29.

crosslinked saponin according to Example 1.33.

For the majority of particles, a stability of more than three months is observed: the color of the particle sediment is unchanged (white or cream), the supernatant is limpid and colorless and microscopic examination shows intact particles.

The stability is more than 4 months for the DHA particles and more than 6 weeks for the particles of crosslinked mannitol.

Particles of crosslinked β-cyclodextrins according to Example 1.1. except that the cyclodextrin concentrations are 7.5% or 5%: a stability of more than three months is observed.

Other particles were prepared according to Example 1 except that the 1 M sodium hydroxide solution was replaced with a carbonate buffer of pH 11, examples being particles of:

crosslinked β-cyclodextrins prepared with 10% or 5% of cyclodextrins: stability of more than 10 weeks.

crosslinked sucrose: stability of more than one month.

crosslinked DHA: stability of more than 3 months.

EXAMPLE 4

Biodegradability Experiments on Particles of Crosslinked Oligosaccharides or Monosaccharides in an Emulsion System of the "Water-In-Oil" Type The particles are prepared as described in Example 1 except that the speed of agitation is increased to 5000 rpm.

a) Degradation of the Particles in Blood Plasma:

Experimental Protocol:

Frozen human plasma (Centre de Transfusion Sanguine de Reims) is used, which is thawed at the time of use. 50 mg of filtered fresh particles are introduced into a test tube and dispersed in 5 ml of blood plasma. The tube is placed in a water bath at 37° C. Magnetic agitation is installed. The degradation is followed under an optical microscope by comparison with a control tube prepared by dispersing 50 mg of particles in a phosphate buffer of pH 7.4.

Results:

Particles of crosslinked β-cyclodextrins: Degradation starts after 5 h. Very copious debris and open particles after 24 h. By comparison, no degradation is found in the control tube containing the buffer of pH 7.4.

Particles of crosslinked sucrose: Degradation starts after 3 h. Very copious debris of particles after 24 h. Degradation very pronounced compared with the control tube, in which the particles are intact.

Particles of crosslinked DHA: Slow degradation causing the appearance of a brown coloration, which is very distinct after 48 h, showing that the released DHA has reacted with the plasma proteins.

Particles of crosslinked glucose: After 1 h the particles lose their spherical shape and become ellipsoidal. A slow degradation is observed. After 24 h small fragments as well as open microcapsules are visible.

Particles of crosslinked mannitol: Degradation starts after 3 h. Very copious debris and open particles after 24 h. No degradation in the control tube.

Particles of crosslinked glucosamine: Slow degradation and presence of debris after 24 h.

Particles of crosslinked saponin: Degradation starts after 2 h: presence of debris. After 24 h all the particles have been degraded into small fragments.

These experiments show that the particles forming the subject of the invention are biodegradable. Whereas they are intact after prolonged incubation in a buffer of pH 7.4, they are generally degraded in blood plasma, showing a sensitivity to the action of the plasmic esterases, which break the ester linkages formed by the crosslinking agent with the hydroxyl groups of the monosaccharides or oligosaccharides or derivatives thereof.

b) Degradation of the Particles of Crosslinked Sucrose by Invertase:

Reagents:

Invertase (Grade V, baker's yeast, SIGMA) used in the form of a 1% dispersion in an acetate buffer of pH 4.9.

Experimental Protocol:

50 mg of filtered fresh particles are introduced into a test tube and 5 ml of the 1% dispersion of invertase in acetate buffer are added. The tube is placed in a water bath at 37° C. Magnetic agitation is installed. The degradation is followed under an optical microscope by comparison with a control tube prepared by dispersing 50 mg of particles in the acetate buffer of pH 4.9.

In addition, the appearance of glucose in the medium is revealed by means of the Clinistix® test (BAYER): the pink coloration of a glucose oxidase test strip turns violet in the presence of glucose.

Result:

After 6 h: start of particle degradation visible under the optical microscope. The Clinistix test is positive: violet coloration, result: +.

After 24 h only a few isolated particles remain intact. The Clinistix test gives a more positive result: the coloration is pure violet, result: ++. The particles of crosslinked sucrose, which remain intact after incubation in the buffer alone, are attacked by the invertase, an enzyme capable of degrading sucrose to glucose and fructose.

EXAMPLE 5

Standard Protocol for the Preparation of Particles of Crosslinked Oligosaccharides or Monosaccharides in an Emulsion System of the "Oil-In-Water" Type a) Preparation of the oily phase to be encapsulated:

0.6 ml of sebacoyl chloride is added to 5.4 ml of olive oil and the ingredients are mixed.

b) Preparation of the aqueous phase:

30 ml of a 20% solution of sucrose in 1 M sodium hydroxide solution are prepared.

c) Emulsification/crosslinking:

The 6 ml of oily mixture are emulsified in the 30 ml of aqueous phase by agitation at 2000 rpm, agitation being maintained for 1 hour.

d) The particles are separated from the reaction medium, for example by centrifugation.

e) Washes:

The particles are washed several times with distilled water.

EXAMPLE 6

Characteristics of Particles of Crosslinked Oligosaccharides or Monosaccharides in an Emulsion System of the "Oil-In-Water" Type Preparation of the Particles The following batches of particles are prepared:

Batch 1: particles of crosslinked sucrose according to Example 5.

Batch 2: particles of crosslinked sucrose according to Example 5 except that the sucrose concentration in the aqueous phase is increased to 30% and the speed to 5000 rpm.

Batch 3: prepared in the same way as batch 1 except that the sucrose is replaced with mannitol (20%) and the speed of agitation is increased to 5000 rpm.

Batch 4: prepared in the same way as batch 2 except that the sucrose is replaced with sorbitol, the concentration is increased to 30% and the speed of agitation is increased to 5000 rpm.

Characteristics of the Particles

In all cases a cream-colored supernatant is obtained which is formed of microcapsules each containing an oil droplet. Microscopic examination shows that all the oil has been encapsulated. The microcapsules appear as spheres with diameters of between 20 and 150 μm, with a distinct gray-colored membrane. A high pressure exerted on the microscope observation slide bursts the microcapsules, releasing the encapsulated oil and enabling the membrane to be observed, which then looks like a torn transparent bag.

Stability Test at 45° C.

The test is conducted on batches 2 and 4 in the manner described in Example 3.

Results: The microcapsules of batch 2 are stable for at least 5 weeks at 45° C. and the microcapsules of batch 4 for at least 3 weeks.

EXAMPLE 7

Characteristics of Microparticles of Crosslinked β-cyclodextrins (β-CD) as a Function of the Manufacturing Parameters 1) Morphology This is studied by optical microscopy and scanning electron microscopy.

Optical Microscopy:

The particles prepared according to Example 1 (10% of β-CD, 2000 rpm) take the form of a white sediment. This is formed of spherical particles with mottled contents and a distinct membrane. With 7.5% of β-CD (NP 143), the particles have a comparable appearance. With 5% of β-CD (NP 50 bis), vesicles with clear contents are obtained.

Replacement of the 1 M sodium hydroxide solution with a buffer of pH 11 again gives spherical particles with granular contents.

Scanning Electron Microscopy:

This examination is carried out on lyophilized particles. Under all the above conditions the examination reveals particles with a continuous membrane which have collapsed because of lyophilization. By way of example, FIG. 1 shows microparticles prepared under the conditions of Example 1. It should be noted that when these lyophilized particles are resuspended in water, they rapidly regain their spherical shape by swelling with water.

2) Size

This is determined by a laser diffraction technique (Coulter LS 200 granulometer, Coultronics). The results are expressed as volume/diameter of the particles (SD).

Results:

| % of β-CD | Aqueous phase | Speed of agitation | Mean size, μm (SD) |
|---|---|---|---|
| 10% | 1 M sodium hydroxide solution | 2000 rpm | 34.26 (22.9) |
| 10% | 1 M sodium hydroxide solution | 5000 rpm | 11.28 (5.98) |
| 7.5% | 1 M sodium hydroxide solution | 2000 rpm | 21.65 (10.6) |
| 7.5% | 1 M sodium hydroxide solution | 5000 rpm | 8.40 (4.25) |
| 5% | 1 M sodium hydroxide solution | 2000 rpm | 20.69 (12) |

As expected, the particle size decreases when the speed of agitation increases. Also, the particle size decreases when the concentration of β-cyclo-dextrins decreases.

3) Infrared Spectrum

Method: The infrared spectra were determined by the KBr disk technique using a Fourier transform infrared spectrometer (BOMEM, MB series).

Figure 2:
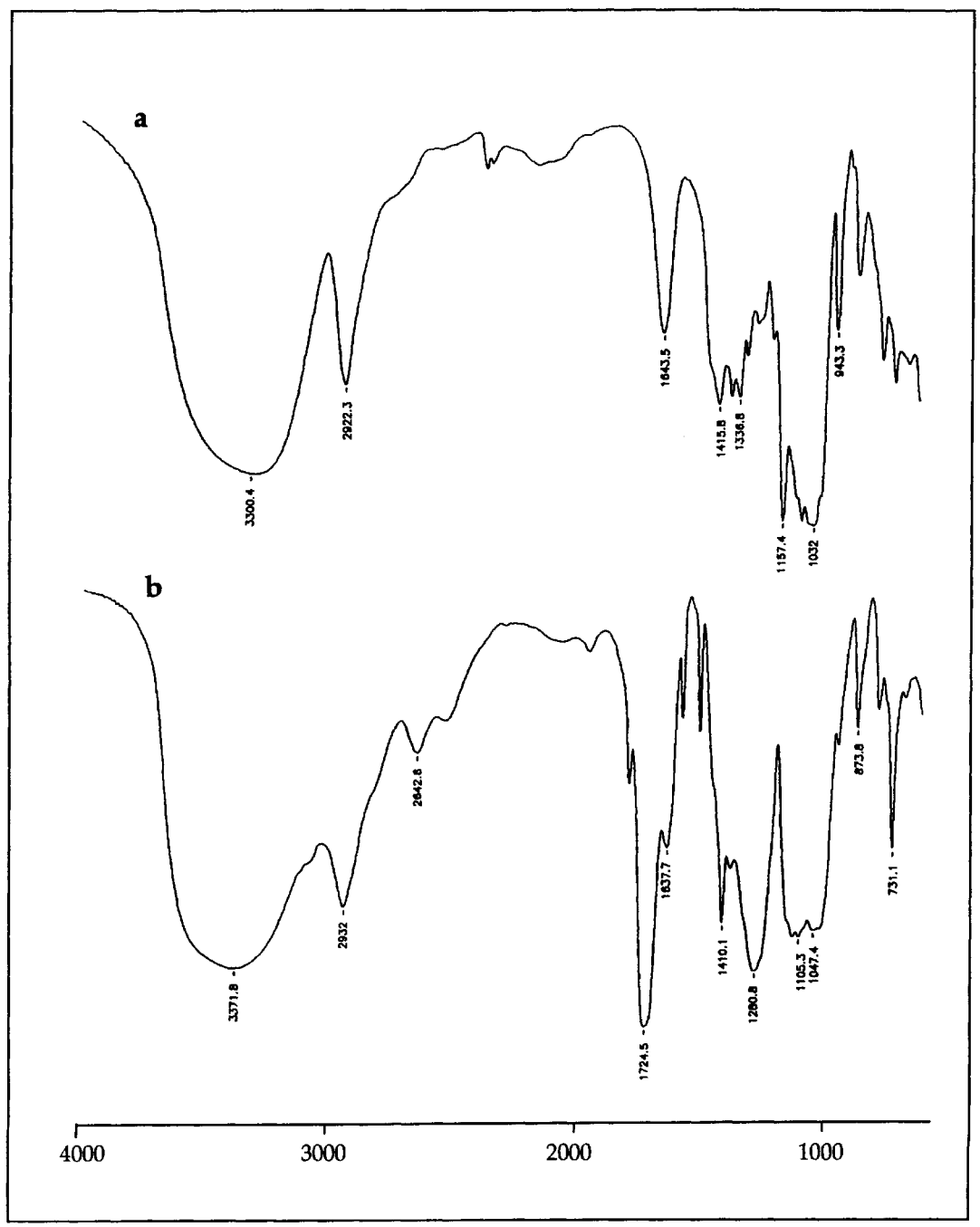
FIG. 2 shows the infrared spectra obtained respectively from non-crosslinked β-cyclodextrins (a) and from particles of crosslinked β-cyclodextrins of the invention prepared from β-cyclodextrins at a concentration of 7.5% using a speed of agitation of 5000 rpm (b), with reference to Example 7.

Results: By way of example, FIG. 2 compares the IR spectrum obtained with non-crosslinked β-CD (spectrum a) and the IR spectrum of particles prepared according to Example 1 except that the β-CD concentration is 7.5% and the speed of agitation is 5000 (spectrum b).

The main differences between the two spectra are the appearance of bands at 1724 $cm^{-1}$, 1280 $cm^{-1}$ and 731 $cm^{-1}$ in the spectrum of the particles (b), reflecting the formation of esters from hydroxyl groups of the β-CD.

4) β-CD Content of the Particles: Determination by Polarimetry

Method:

The amount of β-CD contained in the particles was measured by means of the optical rotation of the β-CD, as described for example by Behar N. et al., (S.T.P. Pharma, 1987, 3, 237–247) in a study pertaining to β-CD fixed to polymers. The first step is complete hydrolysis of the lyophilized particles (60 mg) in 0.5 M sodium hydroxide solution (3 ml) after agitation for 45 min at 20° C. The mixture is neutralized by the addition of 0.25 M HCl and made up to 12 ml with distilled water. The solution (corresponding to 0.5% of particles) is then filtered on a 0.22 μm membrane.

The solution is studied by polarimetry and compared with non-crosslinked β-CD. It was verified with non-crosslinked β-CD that the treatment with 0.5 M sodium hydroxide solution does not modify the results of the polarimetric measurements.

The experiment was carried out on 2 batches of particles prepared according to Example 1 except that the β-CD solution was 7.5% and the speed of agitation was 5000 rpm.

The residual moisture content of these two batches was determined by means of a moisture analyzer (type HR 73 Halogen Moisture Analyzer, Mettler Toledo) so as to relate the results to the weight of dry particles.

Results:

β-CD Content of the Particles (in % of dry weight)

| Batch 1 | 68.7% |
|---|---|
| Batch 2 | 67.4% |
| Mean | 68% |

Thus the particles contain, by weight, 68% of β-CD and 32% of terephthalate, which, related to the molecular weights, correspond to a mean of 3.2 mol of terephthalate per mol of β-CD.

EXAMPLE 8
Evaluation of the Complexation Properties of Particles of Cross-linked β-cyclodextrins Towards Paranitrophenol, and Influence of the Preparative Parameters 1) Complexation Properties of a Reference Batch: Variations in the Sample and the Complexation Time The chosen reference batch is prepared according to Example 1 but with 7.5% of β-cyclodextrins (7.5% of β-CD in 1 M sodium hydroxide solution, speed of agitation: 2000 rpm).

Various samples of microparticles are incubated at 20° C. in a 1 mM solution of paranitrophenol (pNP) buffered to pH 4, with agitation; then, at certain time intervals, the residual pNP in the supernatant is assayed by spectrophotometry until equilibrium is reached. The optical density measurements are used to deduce the residual pNP concentration, from which the amount of pNP fixed by the microcapsules is calculated. This is expressed firstly as a percentage of the initial amount of pNP and secondly in μmol fixed per gram of microcapsules.

Protocol:

Increasing weights of microparticles (10, 20, 50 and 100 mg) are incubated at room temperature in 10 ml of a 1 mM solution of pNP in an acetate buffer of pH 4, for increasing times, with magnetic agitation, in the absence of light. One incubation is carried out per weight and per contact time and each experiment is duplicated. After incubation, the suspension is centrifuged. 2.7 ml of acetate buffer of pH 4 and then 3 ml of 0.25 M sodium hydroxide solution are added to 300 μl of supernatant. The mixture is filtered on a membrane of porosity 0.22 μm. The optical density is measured at 405 nm against a blank prepared without pNP.

The whole experiment is repeated on a new batch of microparticles.

Results:

Fixing of Paranitrophenol by Microparticles of Crosslinked β-CD: Influence of the Sample and the Incubation Time

|  |  | pNP fixed: %/μmol per g of particles* Incubation time | | | | |
|---|---|---|---|---|---|---|
|  |  | 5 min | 10 min | 30 min | 1 h | 24 h |
| Sample | 10 mg | 13/128 | 12/119 | 13/134 | 14/145 | 11/111 |
|  | 20 mg | 19/96 | 20/98 | 21/106 | 24/121 | 21/103 |
|  | 50 mg | 36/72 | 38/76 | 35/69 | 42/83 | 42/83 |
|  | 100 mg | 55/55 | 53/53 | 54/54 | 57/57 | 61/61 |

*Mean of 4 determinations

As expected, when the amounts of microcapsules used increase, so too do the amounts of pNP fixed, expressed in % of the amount initially present. It is also noted that if the amounts of pNP fixed are expressed in μmol per gram of microcapsules, these amounts decrease as the weight of microcapsules used increases: the pNP spreads out more between the particles when their number increases. Finally, it is observed that equilibrium is reached rapidly: the values do not vary greatly after a contact time of 5 min, the plateau being reached after 1 h.

2) Influence of the Preparative Parameters of the Microparticles on the Complexation Properties (with 1 h of incubation)

Protocol:

The following conditions are adopted for this study: sample: 50 mg, incubation time at 20° C.: 1 h. For each parameter studied, the complexation properties of the microcapsules were evaluated on two different batches, two different incubations being carried out for each batch. This made it possible to verify the reproducibility of the results obtained.

The following variations were studied on the reference batch (7.5% of β-CD, 2000 rpm), reproduced twice (batches 1 and 2):

Variations in the concentration of β-CD in the aqueous phase: increase to 10% (batches 3 and 4) and decrease to 5% (batches 5 and 6)

Increase in the speed of agitation to 5000 rpm (batches 7 and 8)

Decrease in the concentration of terephthaloyl chloride to 2.5% (batches 9 and 10).

The mean diameter of all these batches of particles was determined using a Coulter LS 200 granulometer.

Results:

a) Fixing of pNP in 1 h by the Reference Batches: Batches 1 and 2 (7.5% of β-CD; TC: 5%; s: 2000 rpm)

| Batch | Batch 1 | | Batch 2 | |
|---|---|---|---|---|
| Mean size (SD) | 28.02 (17.1) | | 24.8 (13.7) | |
|  | Test 1 | Test 2 | Test 1 | Test 2 |
| pNP fixed: μmol/g | 83.6 | 83.6 | 82.6 | 84.5 |
| Mean of batches 1 and 2 |  |  | 83 |  | b) Fixing of pNP in 1 h by Batches 3 and 4: Increase in the Concentration of β-CD (10% of β-CD; TC: 5%; s: 2000 rpm)

| Batch | Batch 3 | | Batch 4 | |
|---|---|---|---|---|
| Mean size (SD) | 34.2 (22.9) | | 35.3 (20.4) | |
|  | Test 1 | Test 2 | Test 1 | Test 2 |
| pNP fixed: μmol/g | 79.8 | 72.2 | 79.4 | 75.4 |
| Mean of batches 3 and 4 |  |  | 77 |  | c) Fixing of pNP in 1 h by Batches 5 and 6: Decrease in the Concentration of β-CD (5% of β-CD; TC: 5%; s: 2000 rpm)

| Batch | Batch 5 | | Batch 6 | |
|---|---|---|---|---|
| Mean size (SD) | 20.69 (12) | | 22.4 (10) | |
|  | Test 1 | Test 2 | Test 1 | Test 2 |
| pNP fixed: μmol/g | 93.4 | 91.6 | 93.4 | 89.8 |
| Mean of batches 5 and 6 |  |  | 92 |  | d) Fixing of pNP in 1 h by Batches 7 and 8: Increase in the Speed of Agitation (7.5% of β-CD; TC: 5%; s: 5000 rpm)

| Batch | Batch 7 | | Batch 8 | |
|---|---|---|---|---|
| Mean size (SD) | 11.36 (10) | | 10.43 (7.37) | |
|  | Test 1 | Test 2 | Test 1 | Test 2 |
| pNP fixed: μmol/g | 99.0 | 97.0 | 97.4 | 97.6 |
| Mean of batches 7 and 8 |  |  | 98 |  | e) Fixing of pNP in 1 h by Batches 9 and 10: Decrease in the Concentration of Terephthaloyl Chloride to 2.5% (7.5% of β-CD; s: 2000 rpm)

| Batch | Batch 9 | Batch 10 |
|---|---|---|
| Mean size (SD) | 29.53 (14.7) | 30.4 |
| | Test 1 Test 2 | Test 1 Test 2 |
| nPN fixed: µmol/g | 87.6    85.8 | 82.2    84.8 |
| Mean of batches 9 and 10 | 85 | |

Thus, compared with the reference batch, which fixes 83 µmol/g, it is noted that the complexation properties vary with the concentration of β-CD in the aqueous phase: they are reduced (77 µmol/g) for 10% and increased (92 µmol/g) for 5%.

Furthermore, increasing the speed of agitation, which produces microcapsules of smaller size and hence of larger surface area, is a favorable factor (98 µmol/g). On the other hand, lowering the concentration of crosslinking agent to 2.5% does not modify the complexation properties.

EXAMPLE 9

Evaluation of the Complexation Properties of Particles of Crosslinked β-cyclodextrins Towards Propranolol Propranolol is a drug which blocks the adrenergic system. It was chosen for this study because of its high solubility in water and its high affinity for β-CD, due to the fact that the molecule's naphthalene group fits into the hydrophobic cavity of β-CD (Behar et al., S.T.P. Pharma, 1987, 3, 237–247).

Protocol:

β-CD particles were prepared from a 7.5% solution in 1 M sodium hydroxide solution with a speed of agitation of 5000 rpm. The complexation properties were evaluated after agitation of a 10 mg sample of lyophilized particles in 10 ml of a 1 mM or 2 mM solution of propranolol in a phosphate buffer of pH 7.4, in the absence of light. After this contact, the suspension is centrifuged, the supernatant is recovered and the non-fixed propranolol is assayed by UV spectrophotometry at 290 nm. For each of the two concentrations of propranolol, two batches were studied and two tests were carried out per batch. The results are expressed in µmol of propranolol fixed per g of dry microcapsules.

Results:

Propranolol Fixed (in µmol/g) by β-CD Microparticles After 1 h of Incubation in 10 ml of 1 mM or 2 mM Propranolol Solution

| Titer of propranolol solution | 1 mM | | 2 mM | |
|---|---|---|---|---|
| Batch no. | 1 | 2 | 3 | 4 |
| Propranolol fixed (µmol/g) | | | | |
| Test 1 | 509 | 492 | 835 | 794 |
| Test 2 | 495 | 485 | 805 | 811 |
| Mean | 495 | | 811 | |

These results are unchanged if the incubation is prolonged for 2 h or 3 h.

EXAMPLE 10

Reversibility of the Complexation of Propranolol by Particles of Crosslinked β-cyclodextrins, and Re-use The β-CD particles are prepared as described in Example 9 and lyophilized.

Study Protocol:

1) Complexation Step

A 10 mg sample of microcapsules is incubated in 10 ml of a 1 mM solution of propranolol in a phosphate buffer of pH 7.4. After agitation for 1 h, the suspension is centrifuged and the propranolol is assayed in the supernatant.

2) Decomplexation Step

The microparticles which have been centrifuged off are dispersed in 50 ml of phosphate buffer of pH 7.4 and agitated magnetically for 15 min. They are then separated from the medium. The propranolol released into the supernatant is assayed.

The particles are then redispersed in 50 ml of fresh buffer. After magnetic agitation for 15 min, they are separated from the medium and incubated again in 50 ml of fresh buffer. After this treatment, spectrophotometric determination of the propranolol released into the buffer shows that all the propranolol has been released from the complex with the crosslinked β-CD.

3) Re-use of the Microparticles for Further Complexation

The above microparticles from which the propranolol has been removed are incubated again in 10 ml of a 1 mM solution of propranolol in a phosphate buffer of pH 7.4. After agitation for 1 h, the suspension is centrifuged and the propranolol is assayed in the supernatant. The experiment is duplicated.

Results:

Test no. 1:

Amount of propranolol fixed by the 10 mg of particles during complexation step 1: 514 µmol/g of dry particles.

Amount of propranolol fixed by the 10 mg of particles in re-use step 3 after the 3 washes of the decomplexation step: 517 µmol/g.

Test no. 2:

Amount of propranolol fixed by the 10 mg of particles during complexation step 1: 512 µmol/g of dry particles.

Amount of propranolol fixed by the 10 mg of particles in re-use step 3 after the 3 washes of the decomplexation step: 523 µmol/g.

This experiment demonstrates that the β-CD particles can be loaded with a substance and then unloaded and re-used with the same trapping capacity.

EXAMPLE 11

Dialysis Test on a Propranolol Solution Containing Increasing Weights of Particles of Crosslinked β-cyclodextrins: Demonstration of a Slower Release of the Active Principle Behar et al. (S.T.P. Pharma, 1987, 3, 237–247), using propranolol, showed that β-CD fixed to soluble or insoluble polymers made it possible to slow down the diffusion of this active principle through a dialysis membrane, the polymer (and the complex of active principle and β-CD fixed to the polymer) being unable to pass through the membrane.

A comparable experiment was carried out with the microparticles of crosslinked β-CD prepared as in Example 9.

Protocol:

1) Step Involving Complexation of the Propranolol by the Particles

A 10 mg or 50 mg sample of lyophilized microparticles is incubated in 10 ml of a 2 mM solution of propranolol in a phosphate buffer of pH 7.4. Agitation is maintained for 1 h at room temperature, in the absence of light.

2) Study of the Diffusion of the Propranolol Through the Dialysis Membrane

The 10 ml of suspension of β-CD microparticles in the propranolol solution are introduced into a dialysis tube (SPECTRA POR: cellulose ester membrane, molecular cut-off: 5000, diameter: 15 mm) rinsed with phosphate buffer of pH 7.4 beforehand. The tube is closed with 2 clips, the lower one of which is magnetic and enables the system to be agitated. This tube is then placed in a beaker containing 140 ml of phosphate buffer of pH 7.4. The whole is introduced into a water bath at 37° C. and magnetic agitation is started.

Samples of the release medium are taken at regular time intervals so that the propranolol which has diffused can be assayed by UV spectrophotometry at 290 nm. After the assay, the sample is reintroduced into the medium in order to keep the volume constant at 140 ml.

Three determinations are made for each of the two samples of particles: 10 mg and 50 mg. The results are expressed as mean percentages (with standard deviation) of propranolol released, based on the amount introduced into the dialysis tube. A series of 3 tests is also carried out on propranolol without the addition of microparticles (control test).

Results:
Diffusion of Propranolol Through the Dialysis Membrane and Effect of Adding β-CD Particles

|  | % propanolol released: mean value (standard deviation) after: | | | | | | | | | |
| --- | --- | --- | --- | --- | --- | --- | --- | --- | --- | --- |
|  | 30 min | 1 h | 1 h 30 min | 2 h | 3 h | 4 h | 5 h | 6 h | 7 h | 8 h |
| Control without particles | 21.1 (2) | 37.8 (1.5) | 50.1 (1.6) | 60.2 (0.7) | 74.7 (0.5) | 82.2 (0.6) | 87.1 (0.7) | 90 (0.7) | 91.7 (0.5) | 93.3 (0.2) |
| 10 mg of particles | 12.9 (0.6) | 24.2 (0.5) | 33 (0.7) | 40.9 (1.2) | 52.6 (1.7) | 59.7 (1.9) | 65.1 (1.8) | 68.9 (2.1) | 71.7 (2.5) | 74 (2.6) |
| 50 mg of particles | 3.5 (0.4) | 6.9 (0.3) | 10.2 (0.4) | 13.1 (0.7) | 17.9 (0.6) | 22.8 (0.8) | 25.8 (0.6) | 28.5 (0.8) | 31.3 (0.9) | 33.5 (1.1) |

Figure 3:
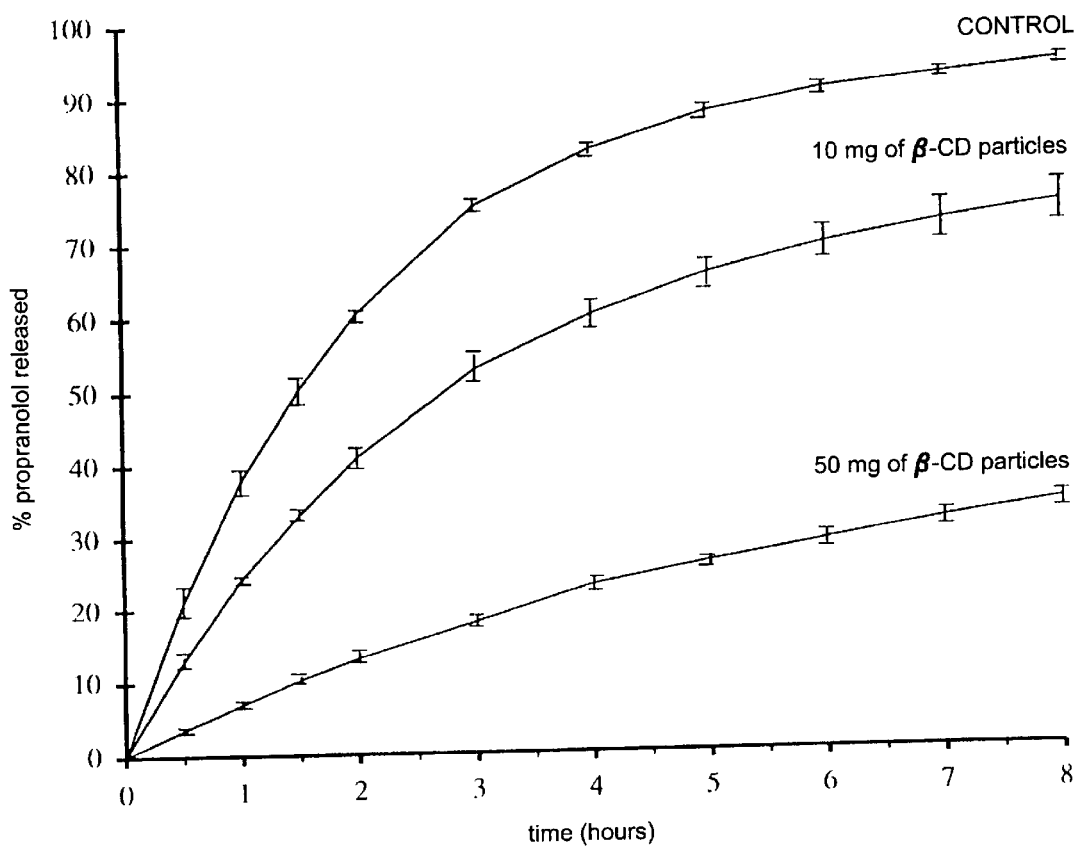
FIG. 3 shows the results of an experiment on the diffusion of propranolol through a dialysis membrane such as that described in Example 11. This Figure combines three curves representing the amounts of propranolol released at different times and expressed as a percentage of the initial amount, one of these curves corresponding to an experiment performed without the addition of β-cyclodextrin particles (control) and the other two corresponding to two experiments performed with the respective addition of 10 mg or 50 mg of particles of crosslinked β-cyclodextrins of the invention.

The data obtained can be used to plot the release curves of FIG. 3.

This series of experiments shows that the particles of crosslinked β-CD do indeed make it possible to slow down the diffusion of a very soluble molecule through a semipermeable membrane in proportion to the amount of particles. Thus, after 6 h, the control has released 90% of the propranolol whereas the tests with 10 mg and then 50 mg of particles released 68.9% and 28.5% of the propranolol, respectively.

EXAMPLE 12
Demonstration of a Slower Release of a Tracer, Methylene Blue, Encapsulated with Increasing Weights of Particles of Crosslinked β-cyclodextrins in Microcapsules of Crosslinked Serum Albumin On the basis of the foregoing results, a novel system for slower release was prepared. Here the dialysis membrane is replaced with the semipermeable membrane of microcapsules of crosslinked protein. The microparticles of β-CD are therefore encapsulated with the chosen tracer, methylene blue.

Protocol: 1) Preparation of the Control Batches of Microcapsules of Crosslinked Serum Albumin Human serum albumin (HSA) is used.
Preparation of the aqueous phase: 10 mg of methylene blue (FLUKA) are dissolved in 10 ml of acetate buffer of pH 7.4. 1 g of HSA is then dissolved in this solution.
Emulsification: The 10 ml of aqueous phase are dispersed in 50 ml of cyclohexane containing 2% of Span 85. The dispersion is agitated for 5 min at 2000 rpm.
Crosslinking: 60 ml of a 2.5% solution of terephthaloyl chloride in cyclohexane are added. The mixture is agitated for 30 min at 2000 rpm. The microcapsules are then centrifuged off and washed 4 times with cyclohexane, the cyclohexane is removed by evaporation on a rotary evaporator and the microcapsules are frozen and lyophilized.
Result: attractive, perfectly round, blue microcapsules with a thick membrane and a size of 10 to 60 μm. After lyophilization, 2 g of a fine powder formed of intact microcapsules are obtained; this powder disperses perfectly in aqueous media.

2) Preparation of Batches of Microcapsules of Crosslinked HSA Containing Increasing Amounts of β-CD Microparticles
  a) Incubation:
  A variable sample (20 mg, 50 mg or 100 mg) of β-CD microparticles prepared as in Example 9 and lyophilized is dispersed in 10 ml of a 0.1% solution of methylene blue in acetate buffer of pH 7.4. Agitation is maintained for 1 h at room temperature, in the absence of light.
  b) Encapsulation in Microcapsules of Crosslinked HSA:
  Preparation of the aqueous phase: 1 g of HSA is dissolved in the 10 ml of the above suspension of β-CD particles after 1 h of incubation.
  Emulsification: The 10 ml of aqueous phase are dispersed in 50 ml of cyclohexane containing 2% of Span 85. The dispersion is agitated for 5 min at 2000 rpm.
  Crosslinking: 60 ml of a 2.5% solution of terephthaloyl chloride in cyclohexane are added. The mixture is agitated for 30 min at 2000 rpm.

The microcapsules are then centrifuged off and washed 4 times with cyclohexane, the cyclohexane is removed by evaporation on a rotary evaporator and the microcapsules are frozen and lyophilized.

Result: Attractive blue microcapsules are obtained. Microscopic observation shows that they are perfectly spherical with a thick membrane and a size of 10 to 70 μm, and that they contain the β-CD microparticles strongly colored by the methylene blue. There is total encapsulation of these microparticles, irrespective of the sample (20 mg, 50 mg or 100 mg of β-CD microparticles).

After lyophilization, 2 g to 2.1 g of a fine powder formed of intact microcapsules are obtained; this powder disperses perfectly in aqueous media.

3) Preparation of Batches of Microcapsules of Crosslinked HSA Containing 50 mg of Non-crosslinked β-CD For comparison, 3 batches of microcapsules were prepared by adding 50 mg of non-crosslinked β-CD instead of particles of crosslinked β-CD to the methylene blue solution. As described above, agitation is maintained for 1 h at room temperature. The encapsulation, separation and drying are then carried out as described above.

It should be noted that the methylene blue/β-CD complex absorbs at the same wavelength as the free methylene blue.

Furthermore, it was verified that, after 1 h of incubation, the mixture containing the methylene blue and the 50 mg of β-CD has the same absorbance as that measured without the addition of β-CD.

4) Methylene Blue Release Tests

Protocol:

A rotating blade dissolution apparatus is used (ERWEKA apparatus in compliance with the Pharmacopoeia); it is thermostatted at 37° C. and the speed of rotation of the blade is 50 rpm.

The entire batch of lyophilized microcapsules is dispersed in 500 ml of phosphate buffer of pH 7.4. At regular time intervals, 5 ml samples of the suspension are taken and centrifuged. The supernatant is filtered on a membrane of porosity 0.2 μm. The optical density of the filtrate is measured at 668 nm. The microcapsules sedimented in the centrifuge tube are resuspended in 5 ml of phosphate buffer and reintroduced into the release medium. Each release test (control test, tests with 20 mg, 50 mg and 100 mg of β-CD particles, test with 50 mg of non-crosslinked β-CD) is carried out in triplicate.

Results:

The amounts of methylene blue released by these different batches of microcapsules after different times, expressed in % of the amount used in the test, are collated in the Table below.

% Methylene Blue Released [mean (standard deviation)] From Microcapsules of Crosslinked HSA and Effect of Adding β-CD Particles or Non-crosslinked β-CD:

complexed, thereby reducing the proportion of tracer which is capable of binding to the protein in the microcapsules. The release rate is therefore slightly increased.

It is concluded from this that, whereas the non-crosslinked β-CD cannot slow down the diffusion of the tracer, insolubilization of the β-CD in the form of microparticles of crosslinked β-CD brings a decisive advantage by making it possible to slow down the release rate of soluble substances in proportion to the amount of microparticles incorporated.

EXAMPLE 13

Particles of Crosslinked DRA: in vitro Tests on Combination with Amino Acids

1) Preparation of Microparticles of Crosslinked DHA

Microparticles of crosslinked DHA are prepared as described in Example 1 except that the 1 M sodium hydroxide solution is replaced with a carbonate buffer ofpH 11 and:

the speed of agitation is kept at 2000 rpm (batch 1)

the speed of agitation is increased to 5000 rpm (batch 2)

the speed of agitation is increased to 5000 rpm and the DHA concentration is reduced to 5% (batch 3).

2) In vitro Test on Combination with Amino Acids

Principle of the Tests:

It has been observed that microcapsules of crosslinked DHA can dissolve gradually in mixtures containing on the one hand dilute disodium carbonate solution (for example 1%) and on the other hand a polyethylene glycol such as PEG 200. The process involves alcoholysis of the ester

| Time | Control without particles | 20 mg of particles | 50 mg of particles | 100 mg of particles | 50 mg of β-CD |
|---|---|---|---|---|---|
| 15 min | 7.21 (0.22) | 5.66 (0.06) | 4.36 (0.13) | 3.22 (0.19) | 8.89 (0.12) |
| 30 min | 9.43 (0.14) | 7.12 (0.17) | 5.23 (0.08) | 3.68 (0.24) | 11.48 (0.39) |
| 45 min | 11.55 (0.17) | 8.51 (0.07) | 6.14 (0.21) | 4.10 (0.31) | 13.85 (0.36) |
| 1 h | 12.95 (0.25) | 9.61 (0.20) | 6.80 (0.26) | 4.60 (0.48) | 15.56 (0.41) |
| 1 h 15 min | 14.37 (0.20) | 10.55 (0.16) | 7.36 (0.05) | 4.88 (0.23) | 16.61 (0.37) |
| 1 h 30 min | 15.15 (0.11) | 11.11 (0.53) | 7.68 (0.32) | 4.98 (0.13) | 17.44 (0.35) |
| 2 h | 16.11 (0.34) | 12.06 (0.13) | 8.44 (0.20) | 5.28 (0.09) | 19.14 (0.44) |
| 2 h 30 min | 17.79 (0.12) | 12.71 (0.06) | 8.57 (0.21) | 5.28 (0.09) | 20.12 (0.58) |
| 3 h | 18.05 (0.12) | 12.82 (0.19) | 8.79 (0.10) | 5.70 (0.19) | 20.81 (0.51) |
| 4 h | 19.31 (0.19) | 13.84 (0.20) | 9.23 (0.21) | 5.73 (0.37) | 21.89 (0.37) |
| 5 h | 19.83 (0.09) | 14.13 (0.19) | 9.37 (0.09) | 5.81 (0.20) | 22.83 (0.40) |
| 6 h | 20.2 (0.38) | 14.2 (0.09) | 9.57 (0.22) | 5.81 (0.13) | 23.10 (0.44) |
| 8 h | 20.13 (0.43) | 14.21 (0.14) | 9.79 (0.05) | 6.06 (0.28) | 23.27 (0.40) |

Figure 4:
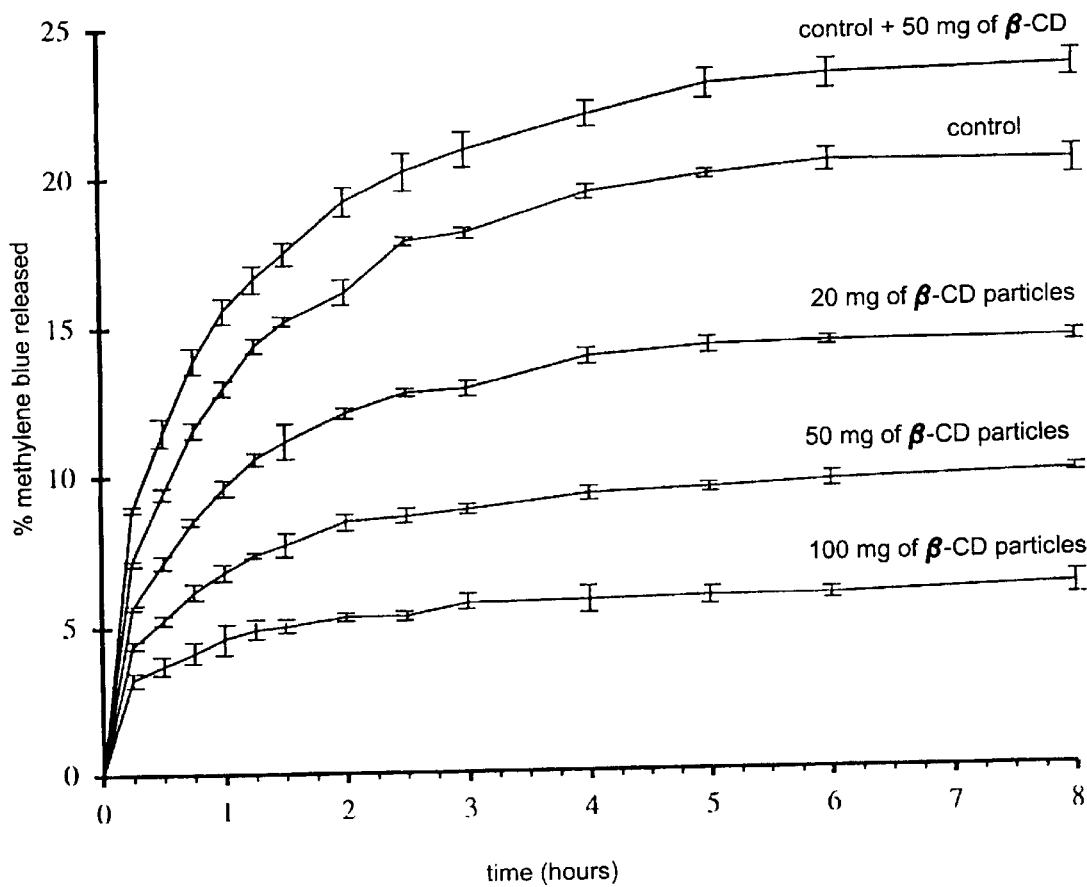
FIG. 4 shows the results of an experiment on the release of methylene blue from microcapsules of crosslinked serum albumin such as that described in Example 12. This Figure combines five curves representing the amounts of methylene blue released at different times and expressed as a percentage of the initial amount (mean values±standard deviations), one of these curves corresponding to an experiment performed without the addition of β-cyclodextrins (control), another corresponding to an experiment performed with the addition of 50 mg of non-crosslinked β-cyclodextrins, and the other three corresponding to three experiments performed with the respective addition of 20 mg, 50 mg or 100 mg of particles of crosslinked β-cyclodextrins of the invention.

The data obtained can be used to plot the release curves shown in FIG. 4. These results, in agreement with the results of the dialysis study of Example 11, show that, after encapsulation in a semipermeable membrane, the particles of crosslinked β-CD do indeed make it possible to obtain a slower release of a water-soluble substance. In this case again, the slowing-down is proportional to the amount of β-CD particles encapsulated.

As expected, the incorporation of non-crosslinked β-CD does not make it possible to slow down the release. In fact, the complex diffuses freely through the membrane of the microcapsules because of its solubility and its low molecular weight. On the contrary, it is seen that, in the presence of non-crosslinked β-CD, the release of methylene blue is more rapid than for the microcapsules of the control batches prepared without adding β-CD. This is doubtless explained by the fact that, in the microcapsules of the control batches, a certain proportion of the tracer fixes to the protein inside the microcapsules, retarding the release. When β-CD is added to the methylene blue solution, some of the tracer is linkages present in the particles, releasing the DHA. This is then capable of reacting with amino acids to give a characteristic brown coloration.

We compared the intensity of the colorations obtained in the presence of glycine using microparticles prepared under the conditions defined above with the intensity obtained using non-crosslinked DHA by reading the optical density at 420 nm after 48 h.

Test Protocol:

Preparation of the experimental tube of microparticles, T1:

20 mg of lyophilized particles are introduced into 4 ml of a mixture composed of 90% v/v of PEG 200 and 10% v/v of 1% disodium carbonate solution.

100 μl of 0.66 M glycine solution are added and the tube is placed in a bath thermostatted at 32° C. After 48 h the mixture is diluted to ¼ with distilled water and the optical density is determined.

Preparation of the tube of microparticles without glycine, T2:

The procedure is the same as for tube T1 except that 100 µl of distilled water are added instead of the glycine solution.

Preparation of the control tube of non-crosslinked DHA with glycine, T3:

The procedure is as for T1 except that the microparticles are replaced with 20 mg of DHA.

Preparation of the control tube of non-crosslinked DHA without glycine, T4:

The procedure is as for T2 except that the microparticles are replaced with 20 mg of DHA.

Results:

These are collated in the Table below:

In vitro Tests on Combinations of Particles of Crosslinked DHA with Glycine: Color, Measurement of the OD After 48 h, Comparison with Free DHA

| | With glycine | | Without glycine | |
|---|---|---|---|---|
| | Color | OD 48 h | Color | OD 48 h |
| Non-crosslinked DHA controls | | | | |
| | 30 min: pale yellow | | 30 min: pale yellow | |
| | 2 h: brown | | | |
| | 48 h: black-brown | 1.169 | 48 h: yellow | 0.154 |
| Microparticles, batch 1 | | | | |
| | 1 h 30 min: brown glint | | 2 h: colorless | |
| | 48 h: orange-brown | 0.494 | 48 h: light yellow | 0.056 |
| Microparticles, batch 2 | | | | |
| | 1 h: brown glint | | 24 h: yellow glint | |
| | 48 h: orange-brown | 0.616 | 48 h: yellow gling | 0.025 |
| Microparticles, batch 3 | | | | |
| | 30 min: brown glint | | 24 h: yellow glint | |
| | 48 h: brown | 0.756 | 48 h: light yellow | 0.081 |

Thus, although producing a lighter coloration than free DHA, the microparticles give rise to the appearance of a brown coloration after 48 h in the presence of glycine. This shows that these particles are capable of releasing DHA, which in turn is capable of combining with amino acids. The microcapsules of batches 2 and 3, which are prepared with a higher speed of agitation and are therefore smaller, give the darkest colorations. The most intense coloration is obtained with the particles prepared with 5% of DHA (batch 3).

EXAMPLE 14

Particles of Crosslinked DHA: Tanning Effect on Reconstructed Skin

The DHA microspheres prepared as described in Example 13 for batch no. 3 were lyophilized and sterilized with 25 kgray of β rays. They were then suspended at a concentration of 2.5% in a sterile medium. Sterile solutions containing DRA concentrations of between 0 and 5% are also prepared.

These two preparations are then applied to reconstructed skin consisting of keratinocytes and normal human fibroblasts inoculated onto the surface of and, respectively, into an extracellular matrix produced by the lyophilization of a collagen gel (Coletica). This reconstructed skin can be used to simulate application to an animal or a human volunteer.

After application of each of the test preparations (10 µl/cm$^2$) to the surface of this reconstructed skin, evaluation of the appearance of the brown color characteristic of the reaction of DHA with amino acids is followed and compared with that of each of the samples of the control range.

After 8, 24, 48 and 96 hours of incubation at 37° C. and under a gaseous $CO_2/O_2$ mixture traditionally used in cell culture, this color is observed and graded.

First of all, it can be seen that the coloration increases throughout the incubation time and that it also increases with the amount of DHA applied to the reconstructed skin. Furthermore, after 96 hours of incubation, it can be seen that the DHA microspheres, used at a concentration of 2.5% in suspension in a sterile medium, systematically enabled reconstructed skin to be colored as intensely as with a 5% solution of DHA. At an identical concentration, the coloring activity obtained with the DHA microspheres is therefore twice as intense as that obtained with DHA used in the free form, which is explained by the DHA being more available when used in the form of microspheres. The sustained release (or delaying effect) obtained with the DHA microspheres consequently provides an explanation of the observed differences in the behavior of the DHA.

These delaying effects make it possible more generally to envisage the use, in these forms of microspheres or nanospheres, of active ingredients which irritate, are toxic, are of low bioavailability or penetrate the cutaneous tissues very rapidly, in cosmetic, pharmaceutical or agri-foodstuff applications.

EXAMPLE 15

Use of the Products of the Invention in Cosmetic or Pharmaceutical Formulations of the Oil-In-Water Emulsion Type Formulation 15a

| | | |
|---|---|---|
| A | Demineralized water | qsp 100 |
| | Butylene glycol | 2 |
| | Glycerol | 3 |
| | Sodium dihydroxycetyl phosphate, isopropyl hydroxycetyl ether | 2 |
| B | Glycerol stearate SE | 14 |
| | Triisononanoin | 5 |
| | Octyl cocoate | 6 |
| C | Butylene glycol, methylparaben, ethylparaben, propylparaben | 2 |
| | pH adjusted to 5.5 | |
| D | Products of the invention | 0.01–10% |

Formulation 15b

| | | |
|---|---|---|
| A | Water | qsp 100 |
| | Butylene glycol | 2 |
| | Glycerol | 3 |
| | Polyacrylamide, isoparaffin, heptaethylene glycol lauryl ether (laureth-7) | 2.8 |
| B | Butylene glycol, methylparaben, ethylparaben, propylparaben | 2 |
| | Phenoxyethanol, methylparaben, propylparaben, butylparaben, ethylparaben | 2 |
| | Butylene glycol | 0.5 |
| C | Products of the invention | 0.01–10% |

Formulation 15c

| | | |
|---|---|---|
| A | Carboxyvinylic polymer (Carbomer) | 0.50 |
| | Propylene glycol | 3 |
| | Glycerol | 5 |
| | Demineralized water | qsp 100 |
| B | Octyl cocoate | 5 |
| | Bisabolol | 0.30 |

|   |                                                                            |         |
|---|----------------------------------------------------------------------------|---------|
|   | Dimethicone                                                                | 0.30    |
| C | Sodium hydroxide                                                           | 1.60    |
| D | Phenoxyethanol, methylparaben, propylparaben, butylparaben, ethylparaben   | 0.50    |
| E | Perfume                                                                    | 0.3     |
| F | Products of the invention                                                  | 0.01–10%|

EXAMPLE 16 OF THE INVENTION

Use of the Products of the Invention in a Formulation of the Water-In-Oil Type

|   |                                                                            |         |
|---|----------------------------------------------------------------------------|---------|
| A | PEG 30 - dipolyhydroxystearate                                             | 3       |
|   | Capric triglycerides                                                       | 3       |
|   | Cetearyl octanoate                                                         | 4       |
|   | Dibutyl adipate                                                            | 3       |
|   | Grape seed oil                                                             | 1.5     |
|   | Jojoba oil                                                                 | 1.5     |
|   | Phenoxyethanol, methylparaben, propylparaben, butylparaben, ethylparaben   | 0.5     |
| B | Glycerol                                                                   | 3       |
|   | Butylene glycol                                                            | 3       |
|   | Magnesium sulfate                                                          | 0.5     |
|   | EDTA                                                                       | 0.05    |
|   | Demineralized water                                                        | qsp 100 |
| C | Cyclomethicone                                                             | 1       |
|   | Dimethicone                                                                | 1       |
| D | Perfume                                                                    | 0.3     |
| E | Product of the invention                                                   | 0.01–10%|

EXAMPLE 17 OF THE INVENTION

Use of the Products of the Invention in a Formulation of the Shampoo or Shower Gel Type

|   |                                                                            |         |
|---|----------------------------------------------------------------------------|---------|
| A | Xanthan gum                                                                | 0.8     |
|   | Demineralized water                                                        | qsp 100 |
| B | Butylene glycol, methylparaben, ethylparaben, propylparaben                | 0.5     |
|   | Phenoxyethanol, methylparaben, propylparaben, butylparaben, ethylparaben   | 0.5     |
| C | Citric acid                                                                | 0.8     |
| D | Sodium laurylsulfate                                                       | 40.0    |
| E | Product of the invention                                                   | 0.01–10%|

EXAMPLE 18 OF THE INVENTION

Use of the Products of the Invention in a Formulation of the Type Comprising Lipstick and Other Anhydrous Products

|   |                                                                            |         |
|---|----------------------------------------------------------------------------|---------|
| A | Mineral wax                                                                | 17.0    |
|   | Isostearyl isostearate                                                     | 31.5    |
|   | Propylene glycol dipelargonate                                             | 2.6     |
|   | Propylene glycol isostearate                                               | 1.7     |
|   | PEG 8 beeswax                                                              | 3.0     |
|   | Palm and palm kernel oil                                                   | 3.4     |
|   | Lanolin oil                                                                | 3.4     |
|   | Sesame oil                                                                 | 1.7     |
|   | Tribehenin                                                                 | 1.7     |
|   | Cetyl lactate                                                              | 1.7     |
|   | Mineral oil, lanolin alcohol                                               | 3.0     |
| B | Castor oil                                                                 | qsp 100 |
|   | Pigments (total)                                                           | 3.9     |
|   | {titanium dioxide, Rouge Covanor W360A ® (Wackherr), Bromo de Phloxine 27 ® (Wackherr), Rouge Covalac W 1510 ® (Wackherr), iron oxides} | |
| C | Product of the invention                                                   | 0.01–5  |

EXAMPLE 19 OF THE INVENTION

Use of the Products of the Invention in an Aqueous Gel Formulation (eye contour gels, slimming gels, etc.)

|   |                                                                            |         |
|---|----------------------------------------------------------------------------|---------|
| A | Demineralized water                                                        | qsp 100 |
|   | Carboxyvinylic polymer (Carbomer)                                          | 0.5     |
|   | Butylene glycol                                                            | 15      |
|   | Phenoxyethanol, methylparaben, propylparaben, butylparaben, ethylparaben   | 0.5     |
| B | Product of the invention                                                   | 0.01–10 |

EXAMPLE 20

Toxicological Studies Carried Out on the Products of the Invention a) Oral Toxicity The test protocol used was consistent with the OECD guideline relating to the study of acute oral toxicity (no. 401 of Feb. 24th, 1987), at maximum doses of 5 g/kg body weight, and the tests caused no macroscopic lesions attributable to a toxic effect of the product.

When used orally at a dose below 5 g/kg, the products of the invention (Example 1) therefore have zero toxicity.

b) Eye Irritation

The tests were performed by the official method according to the decree of May 3rd, 1990 (Journal Officiel de la République Francaise of Nov. 14th, 1990) with the products of the invention (Example 1) and caused no lesions of the iris or cornea.

The products of the invention (Example 1), instilled pure, appeared to be non-irritant and the eye tolerance can be considered to be very good.

c) Skin Irritation

The tests were performed by the official method according to the decree of Feb. 1st, 1982 (Journal Officiel de la République Francaise of Feb. 21st, 1982) with the products of the invention (Example 1) and caused no irritation phenomena.

The products of the invention (Example 1), applied pure, appeared to be non-irritant and the skin tolerance can be considered to be excellent.

What is claimed is:

1. A particle comprising a crosslinked outer wall formed of one or more saccharide component(s) selected from the group consisting of a monosaccharide, an oligosaccharide, and mixtures thereof, crosslinked by means of interfacial crosslinking in emulsion, between the saccharide component(s) comprising at least one primary alcohol moiety having an acylatable hydroxyl, and a polyfunctional acylating crosslinking agent having at least two acyl moieties, thereby producing ester linkages between the acylatable hydroxyl(s) of the primary alcohol(s) of the monosaccharide or oligosaccharide and the acyl moieties of the polyfunctional acylating agent.

2. The particle of claim 1, wherein the saccharide component has a molecular weight below 5000 daltons and carries at least one primary alcohol moiety.

3. The particle of claim 1, wherein said interfacial crosslinking in emulsion is performed at room temperature and said polyfunctional acylating crosslinking agent is a diacid halide.

4. Particle according to claim 1, wherein the saccharide component is present in the form of a saccharide derivative selected from the group consisting of a polyol resulting from hydrogenation of the aldehydic or ketonic groups of oses, an aldonic acid derived from an aldose, a saccharide lactone, a phosphoric acid ester of an ose, an osamine, an heteroside whose oside moiety consists of one or more oses and contains at least one primary alcohol moiety.

5. Particle of claim 1, wherein the saccharide component is a monosaccharide selected from the group consisting of a ketose, an aldose, a polyol, an osamine, an aldonic acid and a corresponding lactone.

6. Particle of claim 5, wherein the ketose is selected from the group consisting of dihydroxyacetone, erythrulose, ribulose, xylulose, fructose, sorbose and derivatives thereof; the aldose is selected from the group consisting of erythrose, threose, xylose, arabinose, ribose, deoxyribose, glucose, mannose and galactose; the polyol is selected from the group consisting of sorbitol, mannitol, xylitol, arabitol, dulcitol, galactitol, erythritol and threitol; the osamine is selected from the group consisting of glucosamine, galactosamine, glucosamine sulfate and galactosamine sulfate; the aldonic acid is selected from the group consisting of gluconic acid and galactonic acid; and the saccharide lactone is selected from the group consisting of a gluconolactone and a galactonolactone.

7. The particle of claim 1, wherein the oligosaccharide is selected from the group consisting of sucrose, lactose, maltose, cellobiose, trehalose, melibiose, raffinose, a dextrin, a product of the partial hydrolysis of starch, a polyol derived from an oligosaccharide, lactitol, maltitol and a commercial preparation containing polyols obtained by hydrogenating hydrolysis products of the partial hydrolysis of starch.

8. A particle comprising a crosslinked outer wall formed of one or more cyclodextrin component(s) comprising at least one primary alcohol moiety having an acylatable hydroxyl, crosslinked by means of interfacial crosslinking in emulsion between said cyclodextrin component and a polyfunctional acylated crosslinking agent having at least two acyl moieties, thereby producing ester linkages between the acylatable hydroxyl(s) of the primary alcohol(s) of the cyclodextrin component and the acyl moieties of the polyfunctional acylating agent.

9. The particle of claim 8, wherein the cyclodextrin component is selected from the group consisting of an alpha-cyclodextrin, a beta-cyclodextrin, a gamma-cyclodextrin, hydroxyethyl β-cyclodextrin, hydroxypropyl β-cyclodextrin, a branched cyclodextrin, glucosyl β-cyclodextrin, diglucosyl β-cyclodextrin, maltosyl β-cyclodextrin and dimaltosyl -cyclodextrin.

10. The particle of claim 4, wherein the heteroside comprises an oside moiety containing one or more oside units and at least one primary alcohol moiety, and a non-oside or aglycone fraction having a cyclic structure containing one or more aromatic or non-aromatic rings which can include one or more heteroatoms selected from the group consisting of nitrogen, oxygen and sulfur atoms, the heteroside being selected from the group consisting of β-D-xyloside, 4-methylumbelliferyl β-D-xyloside, p-nitrophenyl β-D-xyloside, riboflavin, a natural nucleoside consisting of a ribonucleoside, guanosine, adenosine, uridine and cytidine, a deoxyribonucleoside, deoxyguanosine, deoxyadenosine, deoxycytidine and thymidine, a synthetic antiviral nucleoside, an anticancer nucleoside, a structural analog of a natural nucleoside, an adenosine analog of a natural nucleoside, a deoxycytidine analog of a natural nucleoside, a mononucleotide, a deoxymononucleotide, an oligonucleotide, a deoxyoligonucleotide, an antibiotic of the aminoglycoside group, streptomycin, dihydrostreptomycin, kanamycin, amikacin, dibekacin, tobramycin, neomycin, paromomycin, a saponoside with steroidal aglycone, a saponoside from ivy, a saponoside with triterpene aglycone, a saponoside from Panama bark, a cardiotonic heteroside with steroidal aglycone, and digitoxin.

11. The particle of claim 1, which is a nanoparticle.

12. The particle of claim 1, which is a microparticle.

13. The particle of claim 8, which is a nanoparticle.

14. The particle of claim 8, which is a microparticle.

15. A particle comprising a crosslinked outer wall formed of one or more saccharide component(s) having at least one primary alcohol moiety having an acylatable hydroxyl, crosslinked by means of interfacial crosslinking in emulsion between said saccharide component and a polyfunctional acylating crosslinking agent having at least two acyl moieties, thereby producing ester linkages between the acylatable hydroxyl(s) of the primary alcohol(s) of the saccharide component and the acyl moieties of the polyfunctional acylating agent, said saccharide component being selected from the group consisting of:

a β-Cyclodextrin, a mixture of dextrins commercially available,

Raffinose,

Cellobiose,

Sucrose,

Maltose,

Lactose,

Trehalose,

Dihydroxyacetone (DHA),

D-Fructose,

Sorbose,

D-Ribose,

D-Deoxyribose,

D-Xylose,

Paranitrophenyl beta-D-xyloside,

D-Arabinose,

D-Glucose,

D-Mannose,

D-Galactose,

Xylitol,

Erythritol,

Arabitol,

Sorbitol,

Mannitol,

Dulcitol (galactitol),

Maltitol,

Gluconic acid,

Gluconolactone,

D-Glucosamine,

D-Galactosamine,

D-Glucosamine sulfate,

D-Galactosamine sulfate,

Saponin from soapbark,

Guanosine,

Streptomycin sulfate,

Riboflavin,

Deoxyribonucleic acid from herring sperm,

Uridine, and

Lactitol.

16. The particle of claim 15, wherein said particle is a substantially spherical microparticle with a mean size ranging between 20 and 90 micrometers.

17. The particle of claim 1, which is loaded with an active substance, selected from the group consisting of a cosmetic substance, a pharmaceutical substance, a dietetic substance, an agri-foodstuff substance and an agri-industrial substance.

18. The particle of claim 8, which is loaded with an active substance, selected from the group consisting of a cosmetic substance, a pharmaceutical substance, a dietetic substance, an agri-foodstuff substance and an agri-industrial substance.

19. The particle of claim 15, which is loaded with an active substance, selected from the group consisting of a cosmetic substance, a pharmaceutical substance, a dietetic substance, an agri-foodstuff substance and an agri-industrial substance.

20. The particle of claim 1, which is enclosed in larger biocompatible and biodegradable particles, to give double particles forming a slow release system.

21. The particle of claim 8, which is enclosed in larger biocompatible and biodegradable particles, to give double particles forming a slow release system.

22. The particle of claim 15, which is enclosed in larger biocompatible and biodegradable particles, to give double particles forming a slow release system.

23. The particle of claim 20, wherein said larger biocompatible and biodegradable particles are selected from the group consisting of particles of crosslinked proteins and particles of co-crosslinked proteins and polysaccharides.

24. The particle of claim 21, wherein said larger biocompatible and biodegradable particles are selected from the group consisting of particles of crosslinked proteins and particles of co-crosslinked proteins and polysaccharides.

25. The particle of claim 22, wherein said larger biocompatible and biodegradable particles are selected from the group consisting of particles of crosslinked proteins and particles of co-crosslinked proteins and polysaccharides.

26. The particle of claim 23, wherein the protein is selected from the group consisting of an animal protein; and a vegetable protein extracted from Leguminosae; and the polysaccharide is selected from the group consisting of a glycosaminoglycan, a low-molecular heparin with a molecular weight ranging between about 2000 and 10,000, a cosmetically acceptable heparin salt, a pharmaceutically acceptable heparin salt, a natural gum, a carrageenan, a glucomannan, a galactomannan, amylose, amylopectin, and a hydroxyalkylated polysaccharide, hydroxyethyl starch and hydroxyethyl cellulose and mixtures thereof.

27. The particle of claim 26, wherein said animal protein is selected from the group consisting of collagen, atelocollagen, gelatin, serum albumin, ovalbumin, hemoglobin, a milk protein, casein, a whey protein, lactalbumin, globulin and fibrinogen; and said vegetable protein is extracted from a plant selected from the group consisting of soya, lupin, pea, chick pea, alfalfa, horse bean, lentil, haricot bean, colza, sunflower, wheat, maize, barley, malt, oat and rye.

28. The particle of claim 24, wherein the protein is selected from the group consisting of an animal protein; and a vegetable protein extracted from Leguminosae; and the polysaccharide is selected from the group consisting of a glycosaminoglycan, a low-molecular heparin with a molecular weight ranging between about 2000 and 10,000, a cosmetically acceptable heparin salt, a pharmaceutically acceptable heparin salt, a natural gum, a carrageenan, a glucomannan, a galactomannan, amylose, amylopectin, and a hydroxyalkylated polysaccharide, hydroxyethyl starch and hydroxyethyl cellulose and mixtures thereof.

29. The particle of claim 28, wherein said animal protein is selected from the group consisting of collagen, atelocollagen, gelatin, serum albumin, ovalbumin, hemoglobin, a milk protein, casein, a whey protein, lactalbumin, globulin and fibrinogen; and said vegetable protein is extracted from a plant selected from the group consisting of soya, lupin, pea, chick pea, alfalfa, horse bean, lentil, haricot bean, colza, sunflower, wheat, maize, barley, malt, oat and rye.

30. The particle of claim 25, wherein the protein is selected from the group consisting of an animal protein; and a vegetable protein extracted from Leguminosae; and the polysaccharide is selected from the group consisting of a glycosaminoglycan, a low-molecular heparin with a molecular weight ranging between about 2000 and 10,000, a cosmetically acceptable heparin salt, a pharmaceutically acceptable heparin salt, a natural gum, a carrageenan, a glucomannan, a galactomannan, amylose, amylopectin, and a hydroxyalkylated polysaccharide, hydroxyethyl starch and hydroxyethyl cellulose and mixtures thereof.

31. The particle of claim 30, wherein said animal protein is selected from the group consisting of collagen, atelocollagen, gelatin, serum albumin, ovalbumin, hemoglobin, a milk protein, casein, a whey protein, lactalbumin, globulin and fibrinogen; and said vegetable protein is extracted from a plant selected from the group consisting of soya, lupin, pea, chick pea, alfalfa, horse bean, lentil haricot bean, colza, sunflower, wheat, maize, barley, malt, oat and rye.

32. A composition selected from the group consisting of a foodstuff composition, a cosmetic composition, a pharmaceutical composition and a dermo-pharmaceutical composition, comprising an effective amount of particles as defined in claim 1, in a suitable vehicle therefor.

33. A composition selected from the group consisting of a foodstuff composition, a cosmetic composition, a pharmaceutical composition and a dermo-pharmaceutical composition, comprising an effective amount of particles as defined in claim 8, in a suitable vehicle therefor.

34. A composition selected from the group consisting of a foodstuff composition, a cosmetic composition, a pharmaceutical composition and a dermo-pharmaceutical composition, comprising from 0.1 to 20% by weight of particles as defined in claim 1, based on the final weight of the composition.

35. A composition selected from the group consisting of a foodstuff composition, a cosmetic composition, a pharmaceutical composition and a dermo-pharmaceutical composition, comprising from 0.1 to 20% by weight of particles as defined in claim 8, based on the final weight of the composition.

36. The composition of claim 32, wherein said particles are loaded with an active substance selected from the group consisting of a cosmetic substance, a pharmaceutical substance, a dietetic substance, an agri-foodstuff substance and an agri-industrial substance.

37. The composition of claim 32, wherein said particles are enclosed in larger biocompatible and biodegradable particles to give double particles forming slow release system, which can be administered by any mode of administration, comprising the oral route, parenteral route, rectal route, vaginal route, pulmonary route, cutaneous route, ophtalmic route and nasal route.

38. The composition of claim 33, wherein said particles are loaded with an active substance selected from the group consisting of a cosmetic substance, a pharmaceutical substance, a dietetic substance, an agri-foodstuff substance and an agri-industrial substance.

39. The composition of claim 38, wherein said particles are enclosed in larger biocompatible and biodegradable particles to give double particles forming slow release system, which can be administered by any mode of administration, comprising the oral route, parenteral route, rectal route, vaginal route, pulmonary route, cutaneous route, ophtalmic route and nasal route.

40. A composition selected from the group consisting of a foodstuff composition a cosmetic composition, a pharmaceutical composition and a dermo-pharmaceutical composition, comprising an effective amount of particles as defined in claim 1, in a suitable vehicle therefor; said saccharide component comprising a heteroside, said wall being thus formed of one or more crosslinked heteroside behaving as particulate prodrugs or precursors of the active heteroside(s) and being capable for releasing the active principle in vivo under the action of enzymes comprising esterases, which particles can be administered by any mode of administration and allow protection of the active principle, slow release, improvement of the bioavailability, improvement of the skin tolerance, improvement of the mucosa tolerance, and targeting towards an organ, a tissue, or a vascular territory.

41. A composition selected from the group consisting of a foodstuff composition, a cosmetic composition, a pharmaceutical composition and a dermo-pharmaceutical composition, comprising from 0.1 to 20% by weight of particles as defined in claim 1, based on the total weight of the composition, said saccharide component being selected from the group consisting of a β-Cyclodextrin, a mixture of dextrins commercially available, Raffinose, Cellobiose, Sucrose, Maltose, Lactose, Trehalose, Dihydroxyacetone (DHA), D-Fructose, Sorbose, D-Ribose, D-Deoxyribose, D-Xylose, Paranitrophenyl beta-D-xyloside, D-Arabinose, D-Glucose, D-Mannose, D-Galactose, Xylitol, Erythritol, Arabitol, Sorbitol, Mannitol, Dulcitol (galactitol), Maltitol, Gluconic acid, Gluconolactone, D-Glucosamine, D-Galactosamine, D-Glucosamine sulfate, D-Galactosamine sulfate, Saponin from soapbark, Guanosine, Streptomycin sulfate, Riboflavin, Deoxyribonucleic acid from herring sperm, Uridine, and Lactitol.

42. The composition of claim 41, wherein at least some of said particles are loaded with an active substance selected from the group consisting of a cosmetic substance, a pharmaceutical substance, a dietetic substance, an agri-foodstuff substance and an agri-industrial substance.

43. The composition of claim 42, wherein at least some of said particles are enclosed in larger biocompatible and biodegradable particles to give double particles forming a slow release system.

44. The composition of claim 43, wherein said larger biocompatible and biodegradable particles are selected from the group consisting of particles of crosslinked proteins and particles of co-crosslinked proteins and polysaccharides.

45. A process for the manufacture of particles of small dimensions having a crosslinked outer wall formed by crosslinking of one or more saccharide component(s) having at least one primary alcohol moiety having an acylatable hydroxyl, selected from the group consisting of monosaccharide(s) and oligosaccharide(s), said process comprising:

a) the preparation of an aqueous phase at a pH of between 10.5 and about 14, in which at least one said saccharide component is dissolved;

b) the preparation of a hydrophobic phase essentially immiscible with water and optionally containing a surfactant;

c) the dispersion of the aqueous phase in the hydrophobic phase by agitation so as to form an emulsion of the water-in-oil type;

d) the addition, to the emulsion, of a solution of a polyfunctional acylating agent having at least two acylating moieties, agitation being maintained for a sufficient period of time to crosslink the saccharide component at the interface of the dispersed droplets of said emulsion and thereby to form said particles; and e) optionally the separation of said particles from the reaction medium.

46. The process of claim 45, wherein the saccharide component is a cyclodextrin.

47. A process for the manufacture of particles of small dimensions having a crosslinked outer wall formed by crosslinking of one or more saccharide component(s) having at least one primary alcohol moiety having an acylatable hydroxyl, selected from the group consisting of monosaccharide(s) and oligosaccharide(s), said process comprising:

a) the preparation of an aqueous phase at a pH of between 10.5 and about 14, in which at least one saccharide component is dissolved;

b) the preparation of a hydrophobic phase essentially immiscible with water and containing a polyfunctional acylating crosslinking agent having at least two acylating moieties;

c) the dispersion of the hydrophobic phase in the aqueous phase by agitation so as to form an emulsion of the oil-in-water type, agitation being maintained for a sufficient period of time of the dispersed droplets of said emulsion and thereby to form said particles; and d) optionally the separation of said particles from the reaction medium.

48. The process of claim 47, wherein the saccharide component is a cyclodextrin.

49. A process for the manufacture of particles of crosslinked cyclodextrins of small dimensions enclosed in larger particles, said process comprising the following steps:

a) Firstly particles comprising a crosslinked outer wall of crosslinked cyclodextrins are prepared by interfacial crosslinking of at least one cyclodextrin by a polyfunctional acylating agent having at least two acylating moieties, in an emulsion system and are recovered.

b) These particles are then placed or incubated in an aqueous solution of an active principle with a pH of between about 4.5 and about 8 for a sufficient time to allow the active principle to be trapped by the particles.

c) A protein or a protein/polysaccharide mixture is then dissolved in the suspension of particles, d) The mixture is dispersed by agitation in a hydrophobic phase to give an emulsion of the water-in-oil type.

e) A solution of a polyfunctional acylating agent having at least two acylating moieties is added to the emulsion, agitation being maintained for a sufficient time for larger particles to form around the particles of crosslinked cyclodextrins by acylation of the acylatable functional moieties of the protein or protein/polysaccharide mixture.

f) Optionally the larger particles obtained, containing the intact particles of crosslinked cyclodextrins and active principle partially complexed by the cyclodextrins of the particles of crosslinked cyclodextrins, are separated off.

50. The process of claim 45, wherein the aqueous phase consists of a buffer adjusted to a pH above 10.5, or a solution of an alkaline agent.

51. The process of claim 50, wherein said buffer is selected from the group consisting of a carbonate buffer and a phosphate buffer; and said alkaline agent is sodium hydroxide.

52. The process of claim 45, wherein the concentration of the saccharide component in the aqueous phase is between 3% and 80% by weight thereof.

53. The process of claim 47, wherein the concentration of the saccharide component in the aqueous phase is between 3% and 80% by weight thereof.

54. The process of claim 49, wherein said crosslinked cyclodextrins are prepared by interfacial crosslinking from an aqueous phase at a pH of between 10.5 and about 14 in which the cyclodextrins are dissolved at a concentration ranging between 3% and 80% by weight thereof.

55. The process of claim 45, wherein the polyfunctional acylating crosslinking agent is selected from the group consisting of a diacid dihalide and from a diacid anhydride.

56. The process of claim 55, wherein said diacid dihalide is selected from the group consisting of phthaloyl dihalide, terephthalolyl dihalide, sebacoyl dihalide, glutaryl dihalide, adipoyl dihalide and succinyl dihalide; and said diacid anhydride is an anhydride having as diacid moiety the diacid moiety of the diacid dihalide.

57. A method of cosmetic care which comprises the application, to an appropriate site on a mammal in need therof, of a cosmetically effective amount of particles having a crosslinked outer wall formed by crosslinking of one or more saccharide component selected from the group consisting of monosaccharide(s) and oligosaccharide(s) comprising at least one primary alcohol group, said saccharide component being crosslinked by means of interfacial crosslinking in emulsion, between the saccharide component (s) comprising at least one primary alcohol group, and a polyfunctional acylating crosslinking agent, thereby producing ester linkages between the acylatable hydroxyl group(s) of the primary alcohol(s) of the saccharide component and the acyl groups of the polyfunctional acylating agent.

58. A method of cosmetic care comprising the application, to an appropriate site on a mammal in need thereof, of a cosmetically effective amount of particles as defined in claim 8.

59. A method of pharmaceutical treatment comprising administering to an appropriate site of a mammal in need thereof, of a pharmaceutical effective amount of particles as defined in claim 1 containing a pharmaceutically active substance, in a pharmaceutical acceptable vehicle.

60. A method of pharmaceutical treatment comprising administering to an appropriate site of a mammal in need thereof, of a pharmaceutical effective amount of particles as defined in claim 8 containing a pharmaceutically active substance, in a pharmaceutical acceptable vehicle.

61. A method of pharmaceutical treatment comprising administering to an appropriate site of a mammal in need thereof, of a pharmaceutical effective amount of particles as defined in claim 15, in a pharmaceutical acceptable vehicle.

62. A method of therapeutical treatment comprising administering to an apropriate site on a mammal in need thereof of a pharmaceutically effective amount of particles having a crosslinked outer wall formed by interfacial crosslinking with a polyfunctional acylatin agent of one or more heterosides behaving as particulate prodrugs or precursors of the active heteroside(s) and being capable or releasing the heteroside in vivo under the action of enzymes comprising esterases, which particles can be administered by any mode of administration and allow protection of the heteroside, slow release, improvement of the bioavailibity, improvement of the skin tolerance, improvement of the mucosa tolerance, and targeting towards an organ, a tissue territory, or a vascular territory.

63. The method of claim 57, wherein said particles are loaded with a cosmetically active substance.

64. The method of claim 63, wherein said particles are enclosed in larger biocompatible and biodegradable particles to give double particles forming a slow release system.

65. The method of claim 64, wherein said larger biocompatible and biodegradable particles are selected from the group consisting of crosslinked proteins and particles of co-crosslinked proteins and polysaccharides.

66. The method of claim 58, wherein said particles are loaded with a cosmetically active substance.

67. The method of claim 66, wherein said particles are enclosed in larger biocompatible and biodegradable particles to give double particles forming a slow release system.

68. The method of claim 67, wherein said larger biocompatible and biodegradable particles are selected from the group consisting of crosslinked proteins and particles of co-crosslinked proteins and polysaccharides.

69. The method of claim 59, wherein said particles are loaded with a pharmaceutically active substance.

70. The method of claim 69, wherein said particles are enclosed in larger biocompatible and biodegradable particles to give double particles forming a slow release system.

71. The method of claim 70, wherein said larger biocompatible and biodegradable particles are selected from the group consisting of crosslinked proteins and particles of co-crosslinked proteins and polysaccharides.

72. The method of claim 60, wherein said particles are loaded with a pharmaceutically active substance.

73. The method of claim 72, wherein said particles are enclosed in larger biocompatible and biodegradable particles to give double particles forming a slow release system.

74. The method of claim 73, wherein said larger biocompatible and biodegradable particles are selected from the group consisting of crosslinked proteins and particles of co-crosslinked proteins and polysaccharides.

75. A method of cosmetic care comprising the application, to an appropriate site of a mammal in need thereof, of a cosmetically effective amount of particles as defined in claim 15.

76. The method of claim 75, wherein said particles are loaded with a cosmetically active substance.

77. The method of claim 76, wherein said particles are enclosed in larger biocompatible and biodegradable particles to give double particles forming a slow release system.

78. The method of claim 77, wherein said larger biocompatible and biodegradable particles are selected from the group consisting of crosslinked proteins and particles of co-crosslinked proteins and polysaccharides.

79. The composition of claim 40, wherein the particles further contain an active substance for an antibiotic therapy, an antiviral therapy, an anticancer therapy, or for the transfer of genetic material into cells.

80. The method of claim 62, wherein the particles further contain an active substance for an antibiotic therapy, an antiviral therapy, an anticancer therapy, or for the transfer of genetic material into cells.

* * * * *

UNITED STATES PATENT AND TRADEMARK OFFICE
CERTIFICATE OF CORRECTION

PATENT NO.    : 6,197,757 B1  
DATED         : March 6, 2001  
INVENTOR(S)   : Perrier et al.

Page 1 of 1

It is certified that error appears in the above-identified patent and that said Letters Patent is hereby corrected as shown below:

<u>Title page,</u>
Insert item [73], please indicate the assignee as:

COLETICA  
    Lyon, France

Signed and Sealed this

Eighteenth Day of December, 2001

Attest:

Attesting Officer

JAMES E. ROGAN  
*Director of the United States Patent and Trademark Office*